(12) United States Patent
Jacobson et al.

(10) Patent No.: US 8,735,407 B2
(45) Date of Patent: *May 27, 2014

(54) PURINE DERIVATIVES AS A₃ ADENOSINE RECEPTOR-SELECTIVE AGONISTS

(75) Inventors: Kenneth A. Jacobson, Silver Spring, MD (US); Artem Melman, Potsdam, NY (US)

(73) Assignee: The United States of America, as represented by the Secretary of the Department of Health and Human Services, Washington, DC (US)

(*) Notice: Subject to any disclaimer, the term of this patent is extended or adjusted under 35 U.S.C. 154(b) by 300 days.

This patent is subject to a terminal disclaimer.

(21) Appl. No.: 12/935,461

(22) PCT Filed: Mar. 24, 2009

(86) PCT No.: PCT/US2009/038026
§ 371 (c)(1),
(2), (4) Date: Nov. 1, 2010

(87) PCT Pub. No.: WO2009/123881
PCT Pub. Date: Oct. 8, 2009

(65) Prior Publication Data
US 2011/0046166 A1 Feb. 24, 2011

Related U.S. Application Data

(60) Provisional application No. 61/040,985, filed on Mar. 31, 208.

(51) Int. Cl.
*A61K 31/522* (2006.01)
*C07D 473/00* (2006.01)

(52) U.S. Cl.
USPC ..................................... 514/263.37; 544/276

(58) Field of Classification Search
USPC ........................................ 514/263.4; 544/277
See application file for complete search history.

(56) References Cited

U.S. PATENT DOCUMENTS

| | | | |
|---|---|---|---|
| 5,646,156 A | 7/1997 | Jacobson et al. | |
| 5,688,774 A | 11/1997 | Jacobson et al. | |
| 5,773,423 A | 6/1998 | Jacobson et al. | |
| 5,840,728 A | 11/1998 | Marquez et al. | |
| 6,066,642 A | 5/2000 | Jacobson et al. | |
| 6,187,284 B1 | 2/2001 | Griffiths | |
| 6,197,278 B1 | 3/2001 | Blankenberg et al. | |
| 6,211,165 B1 | 4/2001 | Liang et al. | |
| 6,528,516 B1 | 3/2003 | Civan et al. | |
| 6,586,413 B2 | 7/2003 | Liang et al. | |
| 7,087,589 B2 | 8/2006 | Jacobson et al. | |
| 2003/0143282 A1 | 7/2003 | Fishman | |
| 2003/0216412 A1 | 11/2003 | Jacobson et al. | |
| 2004/0132686 A1 | 7/2004 | Van Tilburg et al. | |
| 2006/0040959 A1 | 2/2006 | Baraldi et al. | |
| 2006/0100168 A1 | 5/2006 | Ravid et al. | |
| 2007/0232626 A1 | 10/2007 | Jacobson et al. | |
| 2011/0046166 A1 | 2/2011 | Jacobson et al. | |
| 2011/0171130 A1* | 7/2011 | Jacobson et al. | 424/1.85 |
| 2012/0184569 A1* | 7/2012 | Jacobson et al. | 514/263.22 |
| 2012/0252823 A1* | 10/2012 | Jacobson et al. | 514/263.4 |
| 2012/0264769 A1* | 10/2012 | Jacobson et al. | 514/263.2 |
| 2012/0270829 A1* | 10/2012 | Salvemini | 514/46 |

FOREIGN PATENT DOCUMENTS

| | | |
|---|---|---|
| EP | 1 798 233 A1 | 6/2007 |
| WO | WO 01/51490 A1 | 7/2001 |
| WO | WO 2006/031505 A1 | 3/2006 |
| WO | WO 2006091905 A1 * | 8/2006 |
| WO | WO 2006/113204 A2 | 10/2006 |
| WO | WO 2006/128159 A2 | 11/2006 |
| WO | WO 2006125190 A1 | 11/2006 |

(Continued)

OTHER PUBLICATIONS

Wermuth, Camille. "Molecular Variations Based on Isoteric Replacements." The Practice of Medicinal Chemistry. Academic Press, 1996. pp. 203-237.*

Bradford, "A Rapid and Sensitive Method for the Quantitation of Microgram Quantities of Protein Utilizing the Principle of Protein-Dye Binding," *Anal. Biochem.*, 72, 248-254 (1976).

Cheng et al., "Relationship between the inhibition constant ($K_i$) and the concentration of inhibitor which causes 50 per cent inhibition ($I_{50}$) of an enzymatic reaction," *Biochem. Pharmacol.*, 22, 3099-3108 (1973).

Fishman et al., "An agonist to the $A_3$ adenosine receptor inhibits colon carcinoma growth in mice via modulation of GSK-3β and NF-κB," *Oncogene*, 23, 2465-2471 (2004).

(Continued)

*Primary Examiner* — Golam M Shameem
*Assistant Examiner* — Laura Daniel
(74) *Attorney, Agent, or Firm* — Leydig, Voit & Mayer, Ltd.

(57) ABSTRACT

Disclosed are (N)-methanocarba adenine nucleosides, e.g., of formula (I) as highly potent $A_3$ adenosine receptor agonists, pharmaceutical compositions comprising such nucleosides, and a method of use of these nucleosides, wherein $R_1$-$R_6$ are as defined in the specification. These nucleosides exhibit similar selectivities as agonists of the $A_3$ versus the $A_1$ receptor for both human and mouse adenosine receptors, and are contemplated for use in the treatment a number of diseases, for example, inflammation, cardiac ischemia, stroke, asthma, diabetes, and cardiac arrhythmias.

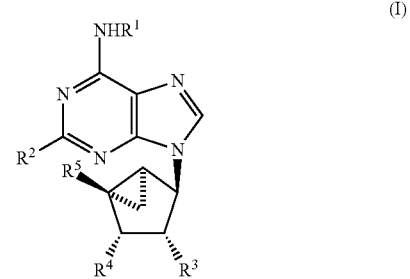

(I)

35 Claims, 3 Drawing Sheets

(56) References Cited

FOREIGN PATENT DOCUMENTS

| WO | WO 2007/002139 A2 | 1/2007 |
|---|---|---|
| WO | WO 2007/009757 A1 | 1/2007 |
| WO | WO 2007/043054 A1 | 4/2007 |
| WO | WO 2007/063538 A1 | 6/2007 |
| WO | WO 2007/086044 A1 | 8/2007 |
| WO | WO 2007/103970 A2 | 9/2007 |
| WO | WO 2007/139775 A2 | 12/2007 |
| WO | WO 2007/139946 A2 | 12/2007 |
| WO | WO 2007/147659 A1 | 12/2007 |
| WO | WO 2008/006369 A1 | 1/2008 |
| WO | WO 2008/023362 A2 | 2/2008 |
| WO | WO 2008/055711 A2 | 5/2008 |
| WO | WO 2008/056361 A1 | 5/2008 |
| WO | WO 2008/058238 A2 | 5/2008 |
| WO | WO 2008/075201 A2 | 6/2008 |

OTHER PUBLICATIONS

Fredholm et al., "International Union of Pharmacology. XXV. Nomenclature and Classification of Adenosine Receptors," *Pharmacol. Rev.*, 53 (4), 527-552 (2001).

Ge et al., "CI-IB-MECA [2-chloro-$N^6$-(3-iodobenzyl)adenosine-5'-N-methylcarboxamide] reduces ischemia/reperfusion injury in mice by activating the $A_3$ adenosine receptor," *J. Pharmacol. Exp. Ther.*, 319 (3), 1200-1210 (2006).

Kim et al., "2-Substitution of $N^6$-Benzyladenosine-5'-uronamides Enhances Selectivity for $A_3$ Adenosine Receptors," *J. Med. Chem.*, 37, 3614-3621 (1994).

Kreckler et al., "Adenosine inhibits tumor necrosis factor-α release from mouse peritoneal macrophages via $A_{2A}$ and $A_{2B}$ but not the $A_3$ adenosine receptor," *J. Pharmacol. Exp. Ther.*, 317 (1), 172-180 (2006).

Lee et al., "Ring-Constrained (N)-Methanocarba Nucleosides as Adenosine Receptor Agonists: Independent 5'-Uronamide and 2'-Deoxy Modifications," *Bioorg. Med. Chem. Lett.*, 11, 1333-1337 (2001).

Liu et al., "Evidence that the adenosine $A_3$ receptor may mediate the protection afforded by preconditioning in the isolated rabbit heart," *Cardiovasc Res.*, 28, 1057-1061 (1994).

Melman et al., "Design of (N)-methanocarba adenosine 5'-uronamides as species-independent $A_3$ receptor-selective agonists," *Bioorg. Med. Chem. Lett.*, 18 (9), 2813-2819 (2008).

Ohta et al., "Role of G-protein-coupled adenosine receptors in downregulation of inflammation and protection from tissue damage," *Nature*, 414, 916-920 (2001).

Ramkumar et al., "The $A_3$ Adenosine Receptor Is the Unique Adenosine Receptor Which Facilitates Release of Allergic Mediators in Mast Cells," *J. Biol. Chem.*, 268, 16887-16890 (1993).

Strickler et al., "Direct Preconditioning of Cultured Chick Ventricular Myocytes," *J. Clin. Invest.*, 98, 1773-1779 (1996).

Tchilibon et al., "(N)-methanocarba 2,$N^6$-Disubstituted Adenine Nucleosides as Highly Potent and Selective $A_3$ Adenosine Receptor Agonists," *J. Med. Chem.*, 48, 1745-1758 (2005).

Von Lubitz et al., "Adenosine $A_3$ receptor stimulation and cerebral ischemia," *Eur. J. Pharmacol.*, 263, 59-67 (1994).

Auchampach et al., "Synthesis and pharmacological characterization of [$^{125}$I]MRS5127, a high affinity, selective agonist radioligand for the $A_3$ adenosine receptor," *Biochem. Pharmacol.*, 79 (7), 967-973 (2010).

Bar-Yehuda et al., "The $A_3$ adenosine receptor agonist CF102 induces apoptosis of hepatocellular carcinoma via de-regulation of the Wnt and NF-κB signal transduction pathways," *Int. J. Oncol.*, 33 (2), 287-295 (2008).

Cordeaux et al., "Agonist-occupied $A_3$ adenosine receptors exist within heterogeneous complexes in membrane microdomains of individual living cells," *FASEB J.*, 22 (3), 850-860 (2008).

Elzein et al., "$N^6$-Cycloalkyl-2-substituted adenosine derivaties as selective, high affinity adenosine $A_1$ receptor agonists," *Bioorg. Med. Chem. Lett.* 17, 161-166 (2007).

Gao et al., "Partial Agonists for $A_3$ Adenosine Receptors," *Curr. Top. Med. Chem.*, 4, 855-862 (2004).

Gao et al., "Structural Determinanats of $A_3$ Adenosine Receptor Activation: Nucleoside Ligands at the Agonist/Antagonist Boundary," *J. Med. Chem.*, 45 (20), 4471-4484 (2002).

Gao et al., "Synthesis and pharmacological characterization of [$^{125}$I]MRS1898, a high-affinity, selective radioligand for the rat $A_3$ adenosine receptor," *Purinergic Signal.*, 5 (1), 31-37 (2009).

Hofer et al., "Homeostatic Action of Adenosine $A_3$ and $A_1$ Receptor Agonists on proliferation of Hematopoietic Precursor Cells," *Exp. Biol. Med.*, 233 (7), 897-900 (2008).

Jacobson et al., "Semi-rational design of (north)-methanocarba nucleosides as dual acting $A_1$ and $A_3$ adenosine receptor agonists: novel prototypes for cardioprotection," *J. Med. Chem. Letters*, 48 (26), 8103-8107 (2005) (with supporting material).

Joshi et al., "Purine derivatives as ligands for $A_3$ adenosine receptors," *Curr. Top. Med. Chem.*, 5 (13), 1275-1295 (2005).

Joshi et al., "A new synthetic route to (North)-methanocarba nucleosides designed as $A_3$ adenosine receptor agonists," *J. Org. Chem.*, 70 (2), 439-447 (2005).

Kiesewetter et al., "Synthesis and characterization of [$^{76}$Br]-labeled high-affinity $A_3$ adenosine receptor ligands for positron emission tomography," *Nucl. Med. Biol.*, 36 (1), 3-10 (2009).

Lasley et al., "The $A_{2a}/A_{2b}$ receptor antagonist ZM-241385 blocks the cardioprotective effect of adenosine agonist pretreatment in in vivo rat myocardium," *Am. J. Physiol. Heart Circ. Physiol.*, 292, H426-H431 (2007).

Melman et al., "Selective $A_3$ Adenosine Receptor Antagonists Derived from Nucleosides Containing a Bicyclo[3.1.0]hexane Ring System," *Bioorg. Med. Chem.*, 16 (18), 8546-8556 (2008).

Morello et al., "CI-IB-MECA inhibits human thyroid cancer cell proliferation independently of A3 adenosine receptor activation," *Cancer Biol. Ther.*, 7 (2), 278-284 (2008).

PCT/US09/38026 International Search Report dated Jul. 8, 2009.

PCT/US09/52439 International Search Report dated Aug. 3, 2010.

Pedata et al., "The role of ATP and adenosine in the brain under normoxic and ischemic conditions," *Purinergic Signal.*, 3 (4), 299-310 (2007).

Takahashi et al., "Effects of adenosine on adhesion molecule expression and cytokine production in human PBMC depend on the receptor subtype activated," *Br. J. Pharmacol.*, 150 (6), 816-822 (2007).

Tosh et al., "Truncated (N)-Methanocarba Nucleosides as A1 Adenosine Receptor Agonists and Partial Agonists: Overcoming Lack of a Recognition Element,", *ACS Med. Chem. Lett.*, 2, 626-631 (2011).

Tosh, "2-Dialkynyl derivatives of (N)-methanocarba nucleosides: 'Clickable $A_3$ adenosine receptor-selective agonists," *Bioorganic & Medicinal Chemistry*, 18(2), 508-517 (2010).

Wan et al., "The $A_3$ adenosine receptor agonist CP-532,903 [$N^6$-(2,5-dichlorobenzyl)-3'-aminoadenosine-5'-N-methylcarboxamide] protects against myocardial ischemia/reperfusion injury via the sarcolemmal ATP-sensitive potassium channel," *J. Pharmacol. Exp. Ther.*, 324 (1), 234-243 (2008).

Wermuth, "Molecular Variations Based on Isosteric Replacements," The Practice of Medicinal Chemistry, *Academic Press*, 203-237 (1996).

Wunderlich et al., "Dual purinergic synaptic transmission in the human enteric nervous system," *Am. J. Physiol. Gastrointest. Liver Physiol.*, 294 (2), G554-G566 (2008).

Zheng et al., "Protective roles of adenosine $A_1$, $A_{2A}$, and $A_3$ receptors in skeletal muscle ischemia and reperfusion injury," *Am. J. Physiol. Heart Circ. Physiol.*, 293(6), H3685-H3691 (2007).

Baraldi et al., "Adenosine Receptor Antagonists: Translating Medicinal Chemistry and Pharmacology into Clinical Utility," *Chem. Rev.*, 108, 238-263 (2008).

* cited by examiner

PURINE DERIVATIVES AS A₃ ADENOSINE RECEPTOR-SELECTIVE AGONISTS

CROSS-REFERENCE TO A RELATED APPLICATION

This application claims the benefit of U.S. Provisional Patent Application No. 61/040,985, filed Mar. 31, 2008, the disclosure of which is incorporated by reference.

BACKGROUND OF THE INVENTION

Extracellular adenosine acts as a local modulator at four subtypes of adenosine receptors, namely, $A_1$, $A_{2A}$, $A_{2B}$, and $A_3$, which are involved in numerous physiological and pathophysiological processes. Fredholm et al., *Pharmacol. Rev.* 2001; 53:527-52. For example, adenosine attenuates the effects of ischemia in the heart and brain. Acting through the $A_{2A}$ adenosine receptor, it suppresses prolonged inflammation; Ohta et al., *Nature* 2001; 414:916-920; and causes vasodilation and inhibits platelet aggregation, thus increasing the amount of oxygen available to an organ under stress. Adenosine agonists selective for the $A_3$ adenosine receptor are of interest as cerebroprotective, cardioprotective, and anticancer agents. von Lubitz et al., *Eur. J. Pharmacol.*, 1994, 263:59-67; Liu et al., *Cardiovasc Res.*, 1994, 28:1057-61; Strickler et al., *J. Clin. Invest.*, 1996, 98:1773-9; Fishman et al., *Oncogene*, 2004, 23:2465-71.

The potential utility of $A_1$ and $A_2$-selective agents in therapeutic applications has been limited by accompanying side effects, given the ubiquitous nature of the $A_1$ and $A_2$ receptors. The distribution of the $A_3$ adenosine receptor, by contrast, is fairly limited, being found primarily in the CNS, brain, testes, and immune system, where it appears to be involved in the modulation of release from mast cells of mediators of the immediate hypersensitivity reaction (Ramkumar et al., *J. Biol. Chem.*, 268, 16887-16890 (1993)). The limited distribution of the $A_3$ adenosine receptor provides a basis for predicting that $A_3$-selective compounds may be more useful than $A_1$- and $A_2$-selective compounds as potential therapeutic agents.

Accordingly, there is a great interest for finding $A_3$ adenosine receptor agonists, as shown by the patenting activity in this area; see, for example, U.S. Pat. Nos. 5,773,423 and 5,688,774; and U.S. Published Patent Application No. 2003/0216412 A1. Therefore, there is a desire for $A_3$ adenosine receptor agonists, especially those that are selective to $A_3$ adenosine receptor over the $A_1$ and $A_2$ adenosine receptors.

BRIEF SUMMARY OF THE INVENTION

The invention provides $A_3$ selective agonists, particularly N-methanocarba adenine nucleosides, for example, with selected substituents at the 2, $N^6$, 2',3',4', and/or 5'-positions, pharmaceutical compositions comprising such nucleosides, and methods of use thereof, for example, in a method for selectively activating an $A_3$ adenosine receptor of a mammal comprising administering to the mammal an effective amount of a nucleoside of the invention. Compounds of the invention exhibit similar selectivities as agonists of the $A_3$ versus the $A_1$ receptor which are species-independent.

DETAILED DESCRIPTION OF THE INVENTION

The present invention is predicated on the concept that adenosine analogues having a ring constraint and optionally having large lipophilic substituents at the C-2 and/or $N^6$-positions would display high selectivity as agonists of the $A_3$ adenosine receptor versus the $A_1$ and $A_{2A}$ adenosine receptors for both human and mouse and/or rat adenosine receptors.

Accordingly, the present invention provides compounds of Formula (1):

wherein:

$R^1$ is selected from the group consisting of $C_1$-$C_6$ alkyl, $C_1$-$C_6$ alkoxy, hydroxyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl)amino]-carbonyl]-$C_1$-$C_6$ alkyl]aniline]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^1$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof, and the alkyl or cycloalkyl portion of $R^1$ is optionally substituted with one or more substituents selected from the group consisting of halo, amino, alkyl, alkoxy, aryloxy, hydroxyalkyl, hydroxyalkenyl, hydroxyalkynyl, aminocarbonylalkoxy, and arylalkoxy, and any combination thereof;

$R^2$ is selected from the group consisting of iodo, $C_1$-$C_{20}$ alkyl, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, $C_1$-$C_{20}$ alkyl $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^2$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkylaminocarbonyl, aminoalkylaminocarbonyl, trialkylsilyl, and any combination thereof; or $R^2$ is selected from the group consisting of amino (alkylamino)$_n$ alkylaminocarbonyl wherein n is 1 to 6, aminoalkylcarbonylaminoalkylaminocarbonyl, aminoalkylaminocarbonyl whose amino end is linked to a label, amino (alkylamino)$_n$ alkylaminocarbonyl wherein n is 1 to 6 whose amino end is linked to a label, and aminoalkylcarbonylaminoalkylaminocarbonyl whose amino end is linked to a label;

$R^3$ and $R^4$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^5$ is selected from the group consisting of $C_1$-$C_3$ alkyl aminocarbonyl, di($C_1$-$C_3$ alkyl) aminocarbonyl, $C_1$-$C_3$ alkylthio $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;

or a pharmaceutically acceptable salt thereof, with the proviso that when $R^2$ is iodo, $R^3$ and $R^4$ are hydroxyl, and $R^5$ is methylaminocarbonyl, $R^1$ is not 3-chlorobenzyl.

The term "aryl" refers to aromatic moieties such as phenyl, naphthyl, anthracenyl, and biphenyl. The term "heterocyclyl" refers to 3-7 membered rings which can be saturated or unsaturated, comprising carbon and one or more heteroatoms such as O, N, and S, and optionally hydrogen; optionally in combination with one or more aromatic rings. Examples of heterocyclyl groups include pyridyl, piperidinyl, piperazinyl, pyrazinyl, pyrolyl, pyranyl, tetrahydropyranyl, tetrahydrothiopyranyl, pyrrolidinyl, furanyl, tetrahydrofuranyl, thiophenyl, tetrahydrothiophenyl, purinyl, pyrimidinyl, thiazolyl, thiazolidinyl, thiazolinyl, oxazolyl, tetrazolyl, tetrazinyl, benzoxazolyl, morpholinyl, thiophorpholinyl, quinolinyl, and isoquinolinyl.

The alkyl, alkoxy, and alkylamino groups can be linear or branched. When an aryl group is substituted with a substituent, e.g., halo, amino, alkyl, hydroxyl, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention.

The term "halo" refers to fluorine, chlorine, bromine, and iodine. Examples of bicycloalkyls include norbornyl, s-endonorbornyl, carbamethylcylopentyl, and bicyclohexyl. An example of a tricycloalkyl is adamantyl.

When a group is substituted with sulfur, a hydrogen atom of the group is replaced with a sulfur atom or an oxidized sulfur atom. The sulfur atom may be monosubstituted with an alkyl or aryl group to form a thiol group, or may be disubstituted with alkyl and/or aryl groups to form a thioether group. When the sulfur atom is oxidized, the oxidized sulfur atom is a part of sulfoxide group or a sulfone group.

In an embodiment, $R^1$ is selected from the group consisting of $C_1$-$C_6$ alkyl, $C_3$-$C_8$ cycloalkyl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_3$-$C_8$ cycloalkyl, and heterocyclyl $C_1$-$C_6$ alkyl, wherein the aryl or heterocyclyl portion of $R^1$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy, and any combination thereof. Preferably, $R^1$ is selected from the group consisting of methyl, cyclopentyl, benzyl, diphenylethyl, phenyl cyclopropyl, diphenyl cyclopropyl, and 2,2-diphenylethyl, wherein the phenyl portion of $R^1$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, and any combination thereof. In a specific embodiment, $R^1$ is benzyl.

In another embodiment, $R^1$ is methyl. In a further embodiment, $R^1$ is cyclopentyl or 7-norbornyl. Other embodiments include those wherein $R^1$ is trans-2-phenyl-1-cyclopropyl or 2,2-diphenylethyl.

A specific example of $R^1$ is benzyl substituted with one or more substituents selected from the group consisting of halo, amino, methyl, methoxy, phenoxy, hydroxymethyl, hydroxypropynyl, carboxypropynyl, alkoxycarbonylpropynyl, aminocarbonyl methoxy, and benzyloxy, and any combination thereof. When the benzyl group is monosubstituted, the substitution can be at the 2-, 3-, or 4-position of the benzyl group, and is preferably at the 3-position of the benzyl group. Specific examples of substituted benzyl groups are 3-chlorobenzyl, 3-bromobenzyl, 3-iodobenzyl, 3-(3-hydroxypropynyl) benzyl, and 2,5-dimethoxybenzyl.

In any of the embodiments discussed above, $R^2$ is preferably selected from the group consisting of iodo, $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, and $C_6$-$C_{14}$ aryl $C_2$-$C_{20}$ alkynyl. More preferably, $R^2$ is $C_2$-$C_{20}$ alkynyl. Optionally, $R^2$ is substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkylaminocarbonyl, aminoalkylaminocarbonyl, trialkylsilyl, and any combination thereof. alkynyl. More preferably, $R^2$ is $C_2$-$C_{20}$ alkynyl. Optionally, $R^2$ is substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkylaminocarbonyl, aminoalkylaminocarbonyl, trialkylsilyl, and any combination thereof. More preferably, $R^2$ is substituted with one or more substituents selected from the group consisting of amino, alkylamino, dialkylamino, carboxy, alkoxycarbonyl, aminocarbonyl, aminoalkylaminocarbonyl, trialkylsilyl, and any combination thereof.

In any of the embodiments discussed above, $R^3$ and $R^4$ are preferably independently selected from the group consisting of hydroxyl, amino, mercapto (i.e., SH), and ureido, and more preferably $R^3$ and $R^4$ are hydroxyl.

In any of the embodiments discussed above, $R^5$ is preferably selected from the group consisting of $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, amino $C_1$-$C_3$ alkyl, hydroxy $C_1$-$C_3$ alkyl, and $C_3$-$C_6$ cycloalkylamino, more preferably $R^5$ is $C_1$-$C_3$ alkyl aminocarbonyl or di($C_1$-$C_3$ alkyl) aminocarbonyl, and even more preferably $R^5$ is methylaminocarbonyl.

Specific examples of the compounds of the invention are compounds wherein $R^1$ is 3-chlorobenzyl, $R^3$ and $R^4$ are hydroxyl, and $R^5$ is methylamino carbonyl, and $R^2$ is ethynyl, 2-trimethylsilylethynyl, 1-pentynyl, 5-carbomethoxy-1-pentynyl, 5-carboxy-1-pentynyl, 5-(2-aminoethyl)aminocarbonyl-1-pentynyl, or iodo; and $R^1$ is 2,5-dimethoxybenzyl, $R^2$ is iodo, $R^3$ and $R^4$ are hydroxyl, and $R^5$ is methylaminocarbonyl.

In accordance with an embodiment, the invention provides a compound of formula I, wherein $R^2$ is selected from the group consisting of carboxyalkylalkynyl, alkoxycarbonylalkylalkynyl, aminoalkylaminocarbonylalkyl alkynyl, amino (alkylamino)$_n$ alkylaminocarbonyl wherein n is 1 to 6, aminoalkylcarbonylaminoalkylaminocarbonyl, aminoalkylaminocarbonyl whose amino end is linked to a label, dye, or reporter group, amino (alkylamino)$_n$ alkylaminocarbonyl wherein n is 1 to 6 whose amino end is linked to a label, dye, or reporter group, aminoalkylcarbonylaminoalkylaminocarbonyl whose amino end is linked to a label, dye, or reporter group, for example, a dye, particularly a fluorescent dye. The label can be a radioactive group such as $^{125}$I.

In a particular embodiment, the invention provides a compound of formula I, wherein $R^1$ is 3-chlorobenzyl, $R^2$ is selected from the group consisting of C≡C(CH$_2$)$_2$COOH, C≡C(CH$_2$)$_4$COOH, C≡C(CH$_2$)$_2$COOCH$_3$, C≡C(CH$_2$)$_4$COOCH$_3$,

$R^3$ and $R^4$ are hydroxyl, and $R^5$ is methylamino carbonyl, or a pharmaceutically acceptable salt thereof.

A specific example of a compound of formula I, wherein $R^1$ is 3-chlorobenzyl and $R^2$ is C≡C(CH$_2$)$_2$CONH(CH$_2$)$_2$NH—CO—(CH$_2$)$_5$Cy5 is compound 44.

human A$_3$ adenosine receptor versus the A$_1$ adenosine receptor of 160 to 6260, while exhibiting K$_i$ values at the mouse A$_3$ adenosine receptor of about 8.7 nM or less, with a selectivity for the mouse A$_3$ adenosine receptor versus the mouse A$_1$ adenosine receptor of 35.6 to 229. Thus, the ratio of A$_3$ to A$_1$ adenosine receptor selectivities for human as compared to mouse adenosine receptors observed for 2-alkynyl, N$^6$-3-chlorobenzyl analogs of the invention ranged from about 1.4 to 5.7. The 2-iodo, N$^6$-3-chlorobenzyl derivative 1 and the 2-iodo, 2,5-dimethoxybenzyl derivative 2 exhibited K$_i$ values at the human A$_3$ adenosine receptor of 3.6 nM and 1.3, respectively, with A$_3$/A$_1$ adenosine receptor selectivities of 610 and 2360, respectively, while the ratio of A$_3$/A$_1$ adenosine receptor selectivities observed in human versus mouse adenosine receptors was 12.1 and 3.4, respectively. Compounds 12, 13, 14, 17-20, 31, 37, and 40 exhibited K$_i$ values at the human A$_3$ AR of about 2 nM or less with selectivities up to about 1900 for the human A$_3$ AR vs the human A$_1$ AR.

By way of contrast, the 2-chloro, N$^6$-3-chlorobenzyl analog 13 exhibited A$_3$/A$_1$ adenosine receptor selectivity for human adenosine receptors that was 87 times greater than observed with mouse adenosine receptors, and exhibited only a 10.3-fold selectivity for A$_3$ versus A$_1$ adenosine receptors for mouse adenosine receptors.

The compounds of formula I provide an advantage that functionalized congeners can be prepared from these com- (44)

Among the N$^6$-3-chlorobenzyl, 5'-N-methylamide substituted compounds of the invention, the 2-ethynyl, N$^6$-3-chlorobenzyl analog 3 displayed K$_i$ values at the human and mouse A$_3$ adenosine receptors of 1.30 nM and 0.85 nM, respectively, while exhibiting selectivities for the A$_3$ versus the A$_1$ adenosine receptors of 134 for human and 53.6 for mouse. Other N$^6$-3-chlorobenzyl analog analogues such as the 2-(2-trimethylsilylethynyl) derivative 4, the 2-(1-pentynyl) derivative 5, the 2-(5-methoxycarbonyl-1-pentynyl) derivative 6, the 2-(5-carboxy-1-pentynyl) derivative 7, and the 2-(5-(2-aminoethyl)aminocarbonyl-1-pentynyl) derivative 8 all exhibited K$_i$ values at the human A$_3$ adenosine receptor of about 2 nM or less, with a selectivity for the pounds. For example, starting from the amine or carboxyl end of $R^2$, various moieties can be attached covalently. Thus, for example, carriers can be covalently attached for enhancing drug delivery. Dendrimers, e.g., PAMAM polyamine dendrimers, such as G3 dendrimers, can be covalently attached to provide multivalent binding. Reporter groups or moieties can be attached for probing distal interactions with adenosine receptors. Spectroscopic probes such as fluorescent probes, ESR probes, or NMR probes can be covalently linked to the amine or carboxyl ends. Other pharmacophores may be covalently linked to the amine or carboxyl ends so that dual acting drugs can be produced, example, an A$_1$ AR agonist can be linked to an A$_3$ AR agonist or a P2Y$_1$, P2Y$_2$, P2Y$_4$, P2Y$_6$, or $P2Y_{11}$ agonist, an M1 receptor antagonist, or an $A_1$ AR antagonist can be linked to an $A_3$ AR agonist. The amine or carboxyl ends could also be covalently linked to amino acids, peptides, nucleic acids, glycosides, and one or more small molecules. Examples of other probes include opioid receptor probes. Examples of fluorescent probes are BODIPY and FITC. Cy3B is another example of a cyanine dye.

The present invention also provides compounds of the formula:

Formula II wherein:

$R^6$ is $C_6$-$C_{14}$ aryl $C_1$-$C_6$ alkyl wherein the $C_6$-$C_{14}$ aryl is substituted with a group represented by C≡C—$(CH_2)_n$—$COR^{11}$ wherein $R^1$ is selected from the group consisting of OH, $OR^{12}$, $NR^{13}R^{14}$, wherein $R^{12}$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl;

$R^{13}$ and $R^{14}$ are independently selected from the group consisting of hydrogen, $C_1$-$C_6$ alkyl, and $(CH_2)_nR^{15}$ wherein $R^{15}$ is $NR^{16}R^{17}$, wherein $R^{16}$ and $R^{17}$ are independently selected from the group consisting of hydrogen, $C_1$-$C_6$ alkyl, and $COR^{18}$ wherein $R^{18}$ is hydrogen or $C_1$-$C_6$ alkyl; wherein n is an integer from 1 to 10;

$R^7$ is selected from the group consisting of bromo, chloro, iodo, $C_1$-$C_{20}$ alkyl, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^7$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkylaminocarbonyl, aminoalkylaminocarbonyl, trialkylsilyl, and any combination thereof;

$R^8$ and $R^9$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^{10}$ is selected from the group consisting of $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl; or a pharmaceutically acceptable salt thereof, with the proviso that when $R^7$ is chloro, $R^8$ and $R^9$ are hydroxyl, and $R^{10}$ is methylaminocarbonyl, $R^6$ is not 3-(3-hydroxypropynyl)benzyl.

In a further embodiment, $R^6$ is benzyl substituted with C≡C—$(CH_2)_n$—$COR^{11}$, wherein n is as defined herein. Preferably, $R^{11}$ is selected from the group consisting of OH, $OR^{12}$, and $NR^{13}R^{14}$. When $R^{11}$ is $OR^{12}$, preferably $R^{12}$ is $C_1$-$C_6$ alkyl.

In another embodiment, $R^{11}$ is $NR^{13}R^{14}$. In a further embodiment, $R^{13}$ and $R^{14}$ are both hydrogen. In another embodiment $R^{13}$ is hydrogen and $R^{14}$ is $(CH_2)_nR^{15}$ wherein $R^{15}$ is $NR^{16}R^{17}$, wherein $R^{16}$ and $R^{17}$ are independently selected from the group consisting of hydrogen, $C_1$-$C_6$ alkyl, and $COR^{18}$ wherein $R^{18}$ is hydrogen or $C_1$-$C_6$ alkyl, and wherein n is defined herein.

In any of the embodiments of Formula II, $R^7$ is preferably selected from the group consisting of chloro, bromo, iodo, $C_1$-$C_{20}$ alkynyl, $C_7$-$C_{12}$ cycloalkyl $C_1$-$C_{20}$ alkynyl, $C_7$-$C_{12}$ bicycloalkyl $C_1$-$C_{20}$ alkynyl, $C_7$-$C_{12}$ bicycloalkenyl $C_1$-$C_{20}$ alkynyl, and $C_6$-$C_{14}$ aryl $C_1$-$C_{20}$ alkynyl. More preferably, $R^7$ is selected from the group consisting of chloro, bromo, and iodo.

In any of the embodiments of Formula II, $R^8$ and $R^9$ are preferably independently selected from the group consisting of hydroxyl, amino, thiol, and ureido, and more preferably $R^8$ and $R^9$ are hydroxyl.

In any of the embodiments of Formula II, $R^{10}$ is preferably selected from the group consisting of $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, amino $C_1$-$C_3$ alkyl, hydroxy $C_1$-$C_3$ alkyl, and $C_3$-$C_6$ cycloalkylamino, more preferably $R^{10}$ is $C_1$-$C_3$ alkyl aminocarbonyl or di($C_1$-$C_3$ alkyl) aminocarbonyl, and even more preferably $R^{10}$ is methylaminocarbonyl.

Specific examples of the compounds of the invention as represented by Formula II are compounds wherein $R^6$ is 3-(5-carboxy-1-pentynyl), $R^7$ is chloro, $R^8$ and $R^9$ are hydroxyl, and $R^{10}$ is methylamino carbonyl; $R^6$ is 3-(5-(2-aminoethyl) aminocarbonyl-1-pentynyl), $R^7$ is chloro, $R^8$ and $R^9$ are hydroxyl, and $R^{10}$ is methylamino carbonyl; and $R^6$ is 3-(5-(2-acetamidoethyl)aminocarbonyl-1-pentynyl), $R^7$ is chloro, $R^8$ and $R^9$ are hydroxyl, and $R^{10}$ is methylamino carbonyl.

Among the 2-chloro, 5'-N-methylamide substituted compounds of the invention, the $N^6$-3-(3-hydroxy-1-propynyl) benzyl derivative 16, the $N^6$-3-(5-carboxy-1-pentynyl)benzyl derivative 9, $N^6$-3-(5-(2-aminoethyl)aminocarbonyl-1-pentynyl)benzyl derivative 10, and the $N^6$-3-(5-(2-acetamidoethyl)aminocarbonyl-1-pentynyl)benzyl derivative 11 exhibited $K_i$ values at the human $A_3$ adenosine receptor of 2.9 nM, 17.1 nM, 5.21 nM, and 2.88 nM, respectively, with a selectivity for the human $A_3$ adenosine receptor versus the $A_1$ adenosine receptor of 900, 19, 52, and 63, respectively, while exhibiting $K_i$ values at the mouse $A_3$ adenosine receptor of 1.94 nM to 14.4 nM. The ratio of $A_3$ to $A_1$ adenosine receptor selectivities for human as compared mouse adenosine receptors observed for 2-chloro, $N^6$-substituted benzyl compounds of the invention were 0.4 to 15.7. All of the inventive compounds were only weakly active at either human or mouse $A_2$ adenosine receptors. This is compared with the 2-chloro, $N^6$-3-chlorobenzyl analog 13 already discussed herein, which exhibited considerably lower $A_3$ to $A_1$ adenosine receptor selectivity with mouse adenosine receptors and a substantially lower $A_3$ to $A_1$ adenosine receptor selectivity for mouse adenosine receptors as compared to human adenosine receptors.

The compounds of the present invention can be prepared by any suitable method. For example, intermediates 22-25 can be prepared by the method of Tchilibon et al., *J. Med. Chem.*, 2005, 48, 1745-1758. (1'S,2'R,3'S,4'S,5'S)-4'-[6-Chloro-2-iodo-purin-9-yl]-2',3'-isopropylidene-bicyclo [3.1.0]hexane-1'-carboxylic acid ethyl ester (22) is reacted with primary amines to introduce $R^1$ at the $N^6$ position of the purine residue via displacement of chloride. Subsequent amination of the 5' ester group generates an N-alkylamide (e.g., N-methylamide) at the 5' position. Sonogashira alkynylation at the C-2 position introduces $R^2$ wherein $R^2$ is alkynyl. Hydrolysis of the isopropylidine group provides target compounds having $R^2$=alkynyl.

(1'S,2'R,3'S,4'S,5'S)-4'-[2,6-Dichloro-purin-9-yl]-2',3'-isopropylidene-bicyclo[3.1.0]hexane-1'-carboxylic acid methyl ester (24) reactes with 3-iodobenzylamine to introduce a 3-iodobenzylamino group at the $N^6$ position of the purine residue via displacement of chloride. Subsequent amination of the 5' ester group generates an N-alkylamide (e.g., N-methylamide) at the 5' position. Sonogashira alkynylation at the 3-position of the phenyl ring followed by hydrolysis of the isopropylidine group provides target compounds having 3-alkynylated benzylamino groups at $N^6$.

Preparation of aminocarbonylalkynyl derivatives proceeds via (a) Sonogashira coupling using alkoxycarbonylalkynes, followed by aminolysis with diaminoethane, to give amides. 2-(Aminoethyl)aminocarbonylalkyne 10 is acylated with, e.g., acetic anhydride, to provide (2-acetamidoethyl)aminocarbonylalkynyl derivative 11. Compounds 31-44 can be prepared following the reaction scheme described in FIG. 3.

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

Examples of pharmaceutically acceptable salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, maleic and arylsulfonic, for example, benzenesulfonic and p-toluenesulfonic, acids.

The pharmaceutically acceptable carrier can be any of those conventionally used and is limited only by chemicophysical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The present invention provides a method for activating $A_3$ adenosine receptors in a cell comprising contacting the cell with an effective amount of one or more of the inventive compounds or a pharmaceutically acceptable salt thereof. The contacting can be in vitro or in vivo. When the contacting is done in vitro, the contacting can be done by any suitable method, many of which are known in the art. For example, the cell can be provided in a culture medium and the inventive compound introduced into the culture medium per se, or as a solution of the compound in an appropriate solvent.

The present invention provides a method of selectively activating $A_3$ adenosine receptors in a mammal, which method comprises administering to a mammal in need of selective activation of its $A_3$ adenosine receptors a therapeutically effective amount, including a prophylactically effective amount, of one or more of the inventive compounds or a pharmaceutically acceptable salt(s) thereof which binds with the $A_3$ receptor so as to stimulate an $A_3$ receptor-dependent response. The compound can be administered acutely or chronically.

The mammal can be any suitable mammal and typically is a human, a mouse, or a rat. Desirably, the inventive compounds exhibit $A_3/A_1$ adenosine receptor selectivity that is less than about 10:1 when determined using human and mouse adenosine receptors.

The method of the present invention has particular usefulness in in vivo applications. For example, $A_3$ adenosine receptor agonists can be used in the treatment of any disease state or condition involving the release of inositol-1,4,5-triphosphate (IP3), diacylglycerol (DAG), and free radicals and subsequent arachidonic acid cascades. Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein chronic prophylactic or therapeutic administration of one of the above-described compounds will prevent the onset of symptoms or will reduce recovery time. Examples of disease states and conditions that may be chronically treated in accordance with the present inventive method include inflammatory disorders, such as vascular inflammation and arthritis, allergies, asthma, wound healing, stroke, cardiac failure, acute spinal cord injury, acute head injury or trauma, seizure, neonatal hypoxia (cerebral palsy; prophylactic treatment involves chronic exposure through placental circulation), chronic hypoxia due to arteriovenous malformations and occlusive cerebral artery disease, ischemia and reperfusion injury in skeletal muscle, severe neurological disorders related to excitotoxicity, Parkinson's disease, Huntington's chorea, and other diseases of the CNS, cardiac disease, kidney disease, and contraception.

The following examples further illustrate the invention but, of course, should not be construed as in any way limiting its scope.

Example 1

$^1$H NMR spectra were obtained with a Varian Gemini 300 spectrometer using $CDCl_3$, $DMSO-d_6$, and $CD_3OD$ as solvents. Chemical shifts are expressed in $\delta$ values (ppm). TLC analysis was carried out on aluminum sheets precoated with silica gel $F_{254}$ (0.2 mm) from Sigma-Aldrich. Low-resolution mass spectrometry was performed with a JEOL™ SX102 spectrometer with 6-kV Xe atoms following desorption from a glycerol matrix or on an AGILENT™ LC/MS 1100 MSD, with a WATERS™ (Milford, Mass.) ATLANTIS™ C18 column. Flash chromatography was performed using silica gel (200-400 mesh, 60 Å, Sigma-Aldrich). High resolution mass spectroscopic (HRMS) measurements were performed on a proteomics optimized Q-TOF-2 (MICROMASS-WATERS™) using external calibration with polyalanine. Observed mass accuracies are those expected based on known performance of the instrument as well as trends in masses of standard compounds observed at intervals during the series of measurements. Reported masses are observed masses uncorrected for this time-dependent drift in mass accuracy.

(1'S,2'R,3'S,4'S,5'S)-4'-[6-Chloro-2-iodo-purin-9-yl]-2', 3'-isopropylidene-bicyclo[3.1.0]hexane-1'-carboxylic acid ethyl ester (22), (1'S,2'R,3'S,4'S,5'S)-4'-[6-(3-Chlorobenzylamino)-2-iodopurin-9-yl]-2',3'-O-isopropylidene bicyclo [3.1.0]hexane-1'-carboxylic N-methylamide (23), (1'S,2'R, 3'S,4'S,5'S)-4'-[2,6-Dichloro-purin-9-yl]-2',3'-isopropylidene-bicyclo[3.1.0]hexane-1'-carboxylic acid methyl ester (24), and (1'S,2'R,3'S,4'S,5'S)-4'-[6-(3-Iodobenzylamino)-2-iodopurin-9-yl]-2',3'-O-isopropylidene bicyclo [3.1.0]hexane-1'-carboxylic N-methylamide (25) were prepared according to a published method. Tchilibon et al., *J. Med. Chem.*, 2005, 48, 1745-1758.

(1'S,2'R,3'S,4'S,5'S)-4'-[6-(2,5-Dimethoxybenzylamino)-2-iodopurin-9-yl]-2',3'-dihydroxybicyclo[3.1.0]hexane-1'-carboxylic acid N-methylamide (2). To a solution of compound 22 (49 mg, 0.1 mmol) in dichloromethane (0.1 mL) was added 2,5-dimethoxybenzylamine (167 mg, 1 mmol). The reaction mixture was left for 16 h at 22° C., transferred to a chromatographic column, and eluted with 30% to 50% ethyl acetate-hexane to afford the corresponding 6-(2,5-dimethoxybenzyl) derivative. The product was dissolved in a 33% solution of methylamine in ethanol and left at room temperature for 48 h. The reaction mixture was evaporated, and the residue was purified by flash chromatography (50% to 100% ethyl acetate-hexane) to afford the corresponding N-methylamide. The product was dissolved in MeOH (3 mL), and TFA (0.3 mL), and water (3 mL) were added, and the reaction mixture was stirred for 16 h at 70° C. The reaction mixture was evaporated, and the residue was purified by flash chromatography (0 to 10% methanol-ethyl acetate) to afford the title compound 2 (10 mg, 21%). $^1$H NMR (CD$_3$OD) 7.94 (s, 1H), 6.98 (d, 1H, J=2.7 Hz), 6.89 (d, 1H, J=9.3 Hz), 6.78 (dd, 1H, J=2.7, 9.0 Hz), 5.09 (d, 1H, J=7.2 Hz), 4.78 (s, 1H), 4.57 (br s, 2H), 3.98 (d, 1H, J=6.6 Hz), 2.88 (s, 3H), 2.01 (m, 1H), 1.78 (t, 1H, J=4.8 Hz), 1.33 (m, 1H). HRMS (ESI MS m/z) Calcd. for C$_{22}$H$_{25}$IN$_6$O$_5$ (M+H)+ 581.10039, found 581.0955.

(1'S,2'R,3'S,4'S,5'S)-4'-[6-Methoxyamino-2-chloropurin-9-yl]-2',3'-dihydroxybicyclo[3.1.0]hexane-1'-carboxylic acid N-methylamide (21). To a solution of compound 24 (20 mg, 0.033 mmol) in dichloromethane (0.1 mL) was added a solution of O-methylhydroxylamine hydrochloride (84 mg, 1 mmol) and triethylamine (101 mg, 1 mmol) in ethanol (0.5 mL). The reaction mixture was left for 16 h at 22° C., diluted with ethyl acetate (30 mL), washed with water, dried, and evaporated. The residue was dissolved in 33% solution of methylamine in ethanol and stirred at room temperature for 48 h. The reaction mixture was evaporated, and the residue was purified by flash chromatography (50% to 100% ethyl acetate-hexane) to afford the corresponding N-methylamide. The product was dissolved in MeOH (3 mL), and TFA (0.3 mL) and water (3 mL) were added. The reaction mixture was stirred for 16 h at 70° C. The reaction mixture was evaporated, and the residue was purified by flash chromatography (0% to 10% methanol-ethyl acetate) to afford the title compound 21 (1.5 mg, 8.5%). $^1$H NMR (CD$_3$OD): 7.45 (s, 1H), 5.07 (d, 1H, J=6.3 Hz), 4.63 (s. 1H), 4.04 (d, 1H, J=6.6 Hz), 3.80 (s, 3H) 2.78 (s, 3H), 2.04 (m, 1H), 1.72 (m, 1H), 1.31 (m, 1H). HRMS (ESI MS m/z) Calcd for C$_{14}$H$_{16}$ClN$_6$O$_4^-$ (M–H$^+$) 367.0927, found 367.0930.

(1'S,2'R,3'S,4'S,5'S)-4'-[6-(3-Chlorobenzylamino)-2-trimethylsilylethynyl-9-yl]-2',3'-dihydroxybicyclo[3.1.0]hexane-1'-carboxylic acid N-methylamide (4). To a solution of (1'S,2'R,3'S,4'S,5'S)-4'-[6-(3-chlorobenzylamino)-2-iodopurin-9-yl]-2',3'-O-isopropylidene bicyclo[3.1.0]hexane-1'-carboxylic N-methylamide 23, 30 mg, 0.05 mmol), dichlorobis(triphenylphosphine)palladium(II) (7 mg, 0.01 mmol), and in DMF (0.05 mL) under nitrogen was added trimethylsilylacetylene (20 mg, 0.20 mmol) and then triethylamine (101 mg, 0.5 mmol). The reaction was stirred at room temperature for 16 h, diluted with ethyl acetate, washed with water, dried, and evaporated. The residue was purified by flash chromatography (30% to 100% ethyl acetate-hexane) to afford the corresponding 2-trimethylsilylethynyl derivative. The product was dissolved in MeOH (3 mL), TFA (0.3 mL) and water (3 mL) were added, and the reaction mixture was stirred for 16 h at 70° C. The reaction mixture was evaporated, and the residue was purified by flash chromatography (0 to 10% methanol-ethyl acetate) to afford the title compound 4 (38%). $^1$H NMR (CD$_3$OD): 8.10 (s, 1H), 7.42 (s, 1H), 7.28 (m, 3H), 4.96 (d, 1H, J=6.6 Hz), 4.7-4.9 (br. m. 3H), 3.97 (d, 1H, J=6.6 Hz) 2.84 (s, 3H), 2.09 (m, 1H), 1.86 (t, 1H, J=5.1 Hz), 1.36 (m, 1H), 0.27 (s, 9H). HRMS (ESI MS m/z) Calcd for C$_{25}$H$_{30}$ClN$_6$O$_3$Si$^+$ (M+H)$^+$ 525.1832, found 525.1837.

(1'S,2'R,3'S,4'S,5'S)-4'-[6-(3-Chlorobenzylamino)-2-(1-pentynyl)-9-yl]-2',3'-dihydroxybicyclo[3.1.0]hexane-1'-carboxylic acid N-methylamide (5). To a solution of (1'S,2'R,3'S,4'S,5'S)-4'-[6-(3-chlorobenzylamino)-2-iodopurin-9-yl]-2',3'-O-isopropylidene bicyclo[3.1.0]hexane-1'-carboxylic N-methylamide (23) (30 mg, 0.05 mmol), dichlorobis(triphenylphosphine)palladium(II) (7 mg, 0.01 mmol), and CuI (1 mg, 0.005 mmol) in DMF (0.05 mL) under nitrogen was added 1-pentyne (14 mg, 0.20 mmol) and then triethylamine (101 mg, 0.5 mmol). The reaction was stirred at room temperature for 16 h, diluted with ethyl acetate, washed with water, dried, and evaporated. The residue was purified by flash chromatography (30% to 100% ethyl acetate-hexane) to afford the corresponding 2-(1-pentynyl) derivative. The product was dissolved in MeOH (3 mL), TFA (0.3 mL) and water (3 mL) were added, and the reaction mixture was stirred for 16 h at 70° C. The reaction mixture was evaporated, and the residue was purified by flash chromatography (0% to 10% methanol-ethyl acetate) to afford the title compound 5. Yield 51%. $^1$H NMR (CD$_3$OD): 8.06 (s., 1H), 7.41 (s, 1H), 7.23-7.30 (m, 3H), 4.99 (d, 1H, J=5.7 Hz), 4.80 (br. s, 3H), 3.96 (d, 1H, J=6.6 Hz), 2.84 (s, 3H), 2.42 (t, 2H, J=7.2 Hz), 2.07 (m, 1H), 1.84 (t, 1H, J=4.5 Hz), 1.65 (sextet, 2H, J=7.2 Hz), 1.36 (m, 1H). HRMS (ESI MS m/z) Calcd for C$_{25}$H$_{28}$ClN$_6$O$_3^+$ (M+H)$^+$ 495.1906, found 495.1911.

(1'S,2'R,3'S,4'S,5'S)-4'-[6-(3-Chlorobenzylamino)-2-(5-methoxycarbonyl-1-pentynyl)-9-yl]-2',3'-dihydroxybicyclo[3.1.0]hexane-1'-carboxylic acid N-methylamide (6) and (1'S,2'R,3'S,4'S,5'S)-4'-[6-(3-chlorobenzylamino)-2-(5-hydroxycarbonyl-1-pentynyl)-9-yl]-2',3'-dihydroxybicyclo[3.1.0]hexane-1'-carboxylic acid N-methylamide (7). To a solution of (1'S,2'R,3'S,4'S,5'S)-4'-[6-(3-chlorobenzylamino)-2-iodopurin-9-yl]-2',3'-O-isopropylidenebicyclo[3.1.0]hexane-1'-carboxylic N-methylamide (23) (30 mg, 0.05 mmol), dichlorobis(triphenylphosphine)palladium(II) (7 mg, 0.01 mmol), and CuI (1 mg, 0.005 mmol) in DMF (0.05 mL) under nitrogen was added methyl co-hexynoate (26 mg, 0.20 mmol) and then triethylamine (101 mg, 0.5 mmol). The reaction was stirred at room temperature for 16 h, diluted with ethyl acetate, washed with water, dried, and evaporated. The residue was purified by flash chromatography (30% to 100% ethyl acetate-hexane) to afford the corresponding 2-(5-methoxycarbonylpentyn-1-yl) derivative. The product was dissolved in MeOH (3 mL), TFA (0.3 mL) and water (3 mL) were added, and the reaction mixture was stirred for 16 h at 70° C. The reaction mixture was evaporated, and the residue was purified by flash chromatography (0% to 10% methanol-ethyl acetate) to afford the title compound 6 (31%). $^1$H NMR (CD$_3$OD): 7.98 (s, 1H), 7.31 (s, 1H), 7.15-7.31 (m, 3H), 4.91 (d, 1H, J=6.9 Hz), 4.70 (br. s, 3H), 3.89 (d, 1H, J=6.6 Hz), 3.57 (s, 3H), 2.75 (s, 3H), 2.44 (m, 4H), 1.98 (m, 1H), 1.84 (m, 2H), 1.75 (m, 1H), 1.27 (m, 1H). HRMS (ESI MS m/z) Calcd for C$_{27}$H$_{30}$ClN$_6$O$_5^+$ (M+H)$^+$ 553.1961, found 553.1970. Further elution with 20% methanol-ethyl acetate provided the title compound 7 (21%). $^1$H NMR (CD$_3$OD): 7.96 (s, 1H), 7.31 (s, 1H), 7.15-7.22 (m, 3H), 4.97 (d, 1H, J=6.6 Hz), 4.75 (br. s., 3H), 3.90 (d, 1H, J=6.6 Hz), 2.76 (s, 3H), 2.41 (t, 2H, J=7.2 Hz), 2.29 (t, 2H, J=7.2 Hz), 1.96 (m, 1H), 1.83 (m, 3H), 1.74 (m, 1H), 1.26 (m, 1H). HRMS (ESI MS m/z) Calcd for C$_{26}$H$_{28}$ClN$_6$O$_5^+$ (M+H)$^+$ 539.1804, found 537.1673.

(1'S,2'R,3'S,4'S,5'S)-4'-[6-(3-Chlorobenzylamino)-2-(1-ethynyl)-9-yl]-2',3'-dihydroxybicyclo[3.1.0]hexane-1'-carboxylic acid N-methylamide (3). To a solution of compound 4 (10 mg) in THF (1 mL) was added 1M solution of tetrabutylammonium fluoride in THF (0.2 mL). The reaction mixture was stirred for 1 h, evaporated, and the residue was purified by flash chromatography (0% to 10% methanol-ethyl acetate) to afford the title compound 3. Yield 75%. $^1$H NMR (CD$_3$OD) 8.1 (s, 1H), 7.41 (d, 1H, J=2.7 Hz), 6.89 (d, 1H, J=9.3 Hz), 6.78 (dd, 1H, J=2.7, 9.0 Hz), 5.06 (d, 1H, J=6.6 Hz), 4.83 (br. s., 2H), 3.99 (d, 1H, J=6.6 Hz), 2.87 (s, 3H), 2.06 (m, 1H), 1.83 (t, 1H, J=4.8 Hz), 1.38 (m, 1H). HRMS (ESI MS m/z) Calcd for C$_{22}$H$_{22}$ClN$_6$O$_3$ (M+H)+ 453.1437, found 453.1444.

(1'S,2'R,3'S,4'S,5'S)-4'-[6-(3-Chlorobenzylamino)-2-[5-(β-aminoethylaminocarbonyl)-1-pentynyl)]-9-yl]-2',3'-dihydroxybicyclo[3.1.0]hexane-1'-carboxylic acid N-methylamide (8). To a solution of ester 6 (2.4 mg, 0.0045 mmol) in methanol (0.05 mL) was added ethylenediamine (1 mL). The reaction mixture was stirred at room temperature for 60 h, and was evaporated to dryness. The residue was purified by flash chromatography (30 to 70% MeOH-EtOAc) to afford the title amide 8 (2.0 mg, 0.0034 mmol, 76%). $^1$H NMR: 7.98 (s, 1H), 7.31 (s, 1H), 7.16-7.22 (m, 3H), 4.92 (d, 1H, J=6.6 Hz), 4.69 (s, 1H), 4.74 (br. s, 2H, under HDO peak) 3.88 (d, 1H, J=6.6 Hz), 3.14 (m, 2H, J=6.3 Hz), 2.75 (s, 3H), 2.63 (t, 2H, J=6.3 Hz), 2.44 (m, 2H), 2.33 (t, 2H, J=7.5 Hz), 1.97 (m, 1H), 1.87 (m, 2H), 1.75 (t, 1H, J=4.8 Hz), 1.28 (m, 1H).

(1'S,2'R,3'S,4'S,5'S)-4'-6-[3-[5-(Methoxycarbonyl)-1-pentynyl]phenylmethylamino]-2-chloro-9-yl}-2',3'-dihydroxybicyclo[3.1.0]hexane-1'-carboxylic acid N-methylamide (26) and (1'S,2'R,3'S,4'S,5'S)-4'-6-[3-[5-(hydroxycarbonyl)-1-pentynyl]phenylmethylamino]-2-chloro-9-yl}-2',3'-dihydroxybicyclo[3.1.0]hexane-1'-carboxylic acid N-methylamide (9). To a solution of compound 25 (60 mg, 0.1 mmol), dichlorobis(triphenylphosphine)palladium(II) (14 mg, 0.02 mmol), and CuI (2 mg, 0.01 mmol) in DMF (0.1 mL) under nitrogen was added methyl co-hexynoate (63 mg, 0.5 mmol) and then triethylamine (202 mg, 1 mmol). The reaction was stirred at room temperature for 16 h, diluted with ethyl acetate, washed with water, dried, and evaporated. The residue was purified by flash chromatography (30% to 100% ethyl acetate-hexane) to afford corresponding 3-(5-methoxycarbonylpentyn-1-yl)phenylaminomethyl derivative. The product was dissolved in MeOH (6 mL), TFA (0.5 mL) and water (2 mL) were added, and the reaction mixture was stirred for 16 h at 70° C. The reaction mixture was evaporated, and the residue was purified by flash chromatography (0% to 10% methanol-ethyl acetate) to afford compounds title methyl ester 27 (28 mg, 0.051 mmol, 51%). $^1$H NMR (CD$_3$OD) 8.04 (s, 1H), 7.39 (s, 1H), 7.24-7.32 (m, 3H), 5.06 (d, 1H, J=6.6 Hz), 4.80 (s, 1H), 4.72 (br. s, 2H), 3.99 (d, 1H, J=6.6 Hz), 3.64 (s, 3H), 2.85 (s, 3H), 2.48 (t, 2H, J=6.9 Hz), 2.45 (t, 2H, J=6.9 Hz), 2.04 (m, 1H), 2.01 (m, 2H), 1.80 (t, 1H, J=5.1 Hz), 1.36 (m, 1H). HRMS (ESI MS m/z) Calcd for C$_{27}$H$_{30}$ClN$_6$O$_5^+$ (M+H)$^+$ 553.1961, found 553.1981. Further elution with 20% MeOH-EtOAc provided the carboxylic acid 9 (12 mg, 0.028 mmol, 22%). $^1$H NMR (DMSOd6) 8.89 (t, 1H, J=6.0 Hz), 8.10 (s, 1H), 7.57 (q, 1H, J=5.2, 4.8), 7.37 (s, 1H), 7.23-7.34 (m, 3H), 5.45 (br s, 1H), 4.94 (d, 1H, J=4.7 Hz), 4.84 (br s, 1H), 4.66 (s, 1H), 4.62 (d, 2H, J=4.8), 3.89 (d, 1H, J=5.1), 2.67 (d, 3H, J=3.9 Hz), 2.44 (t, 2H, J=6.9 Hz), 2.36 (t, 2H, J=8.1 Hz), 1.83 (m, 1H), 1.75 (m, 2H), 1.60 (t, 1H, J=5.2 Hz), 1.30 (m, 1H).

(1'S,1'R,3'S,4'S,5'S)-4'-6-[3-[5-(β-Aminoethylaminocarbonyl)-1-pentynyl]phenylmethylamino]-2-chloro-9-yl}-2',3'-dihydroxybicyclo[3.1.0]hexane-1'-carboxylic acid N-methylamide (10). To a solution of ester 27 (60 mg, 0.11 mmol) in methanol (0.1 mL) was added ethylenediamine (2 mL). The reaction mixture was stirred at room temperature for 60 h, and was evaporated to dryness. The residue was purified by flash chromatography (30 to 70% MeOH-EtOAc) to afford the title amide 10 (57 mg, 0.98 mmol, 88%). $^1$H NMR (CD$_3$OD) 8.14 (s, 1H), 7.51 (s, 1H), 7.15-7.31 (m, 3H), 5.17 (d, 1H, J=7.2 Hz), 4.91 (s, 1H), 4.83 (br. s, 2H) 4.10 (d, 1H, J=6.6 Hz), 3.35 (t, 3H, J=6.0 Hz), 2.96 (s, 3H), 2.82 (t, 2H, J=6.6 Hz), 2.56 (t, 2H, J=6.9 Hz), 2.49 (t, 2H, J=7.8 Hz), 2.16 (m, 1H), 2.01 (m, 2H), 1.91 (t, 1H, J=4.8 Hz), 1.47 (m, 1H). HRMS (ESI MS m/z) Calcd for C28H34ClN8O4+ (M+H)+ 581.2386, found 581.2392.

(1'S,2'R,3'S,4'S,5'S)-4'-6-[3-[5-(β-Acetylaminoethylaminocarbonyl)-1-pentynyl]phenylmethylamino]-2-chloro-9-yl}-2',3'-dihydroxybicyclo[3.1.0]hexane-1'-carboxylic acid N-methylamide (11). To a solution of amine 10 (2 mg, 0.0034 mmol) in methanol (1 mL) was added acetic anhydride (10 mkL, 0.01 mmol). The reaction mixture was stirred for 16 h, evaporated, and the residue was evaporated with dioxane (3×1 mL) to afford compound 11 (2.2 mg, 0.0034 mL, quant. yield). $^1$H NMR (CD$_3$OD) 7.93 (s, 1H), 7.15-7.22 (m, 4H), 4.97 (d, 1H, J=4.8 Hz), 4.70 (s, 1H), 4.62 (br. s, 2H) 3.90 (d, 1H, J=6.6 Hz), 3.16 (s, 4H), 2.76 (s, 3H), 2.36 (t, 2H, J=6.6 Hz), 2.26 (t, 2H, J=7.8 Hz), 1.95 (m, 1H), 1.82 (s, 3H), 1.77 (m, 2H), 1.72 (t, 1H, J=4.8 Hz), 1.28 (m, 1H). HRMS (ESI MS m/z) Calcd for C$_{30}$H$_{36}$ClN$_8$O$_5^+$ (M+H)$^+$ 623.2492 Found 623.2501.

Figure 1:
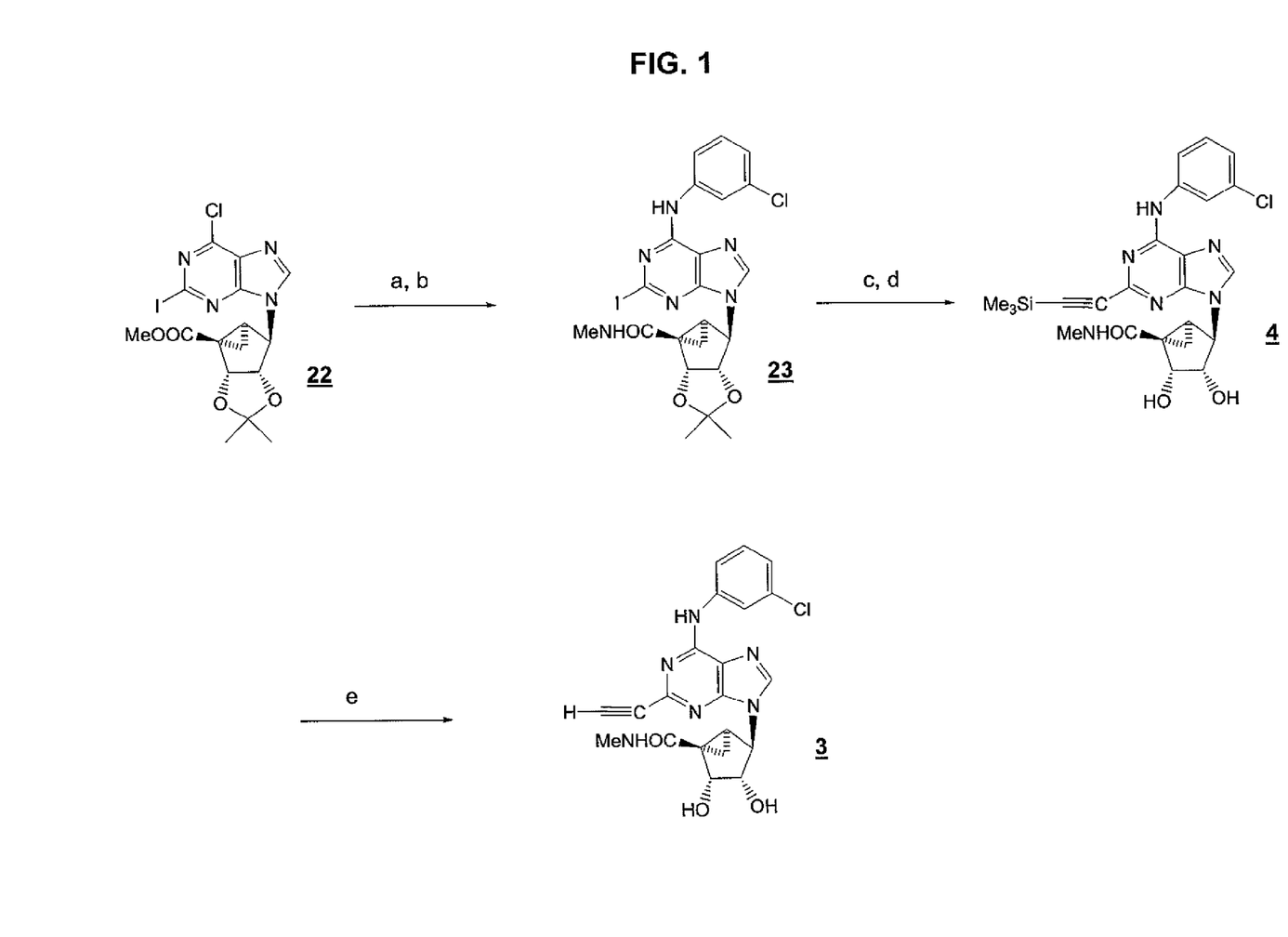
FIG. 1 depicts a reaction scheme for the synthesis of compounds 3 and 4 in accordance with an embodiment of the invention. Reagents and conditions: (a) 3-chlorobenzylamine; (b) $MeNH_2$, EtOH; (c) $Me_3SiC{\equiv}CH$, $PdCl_2(PPh_3)_2$, CuI, DMF, $Et_3N$; (d) TFA, MeOH, $H_2O$; (e) n-$Bu_4NF$, THF.
Figure 2:
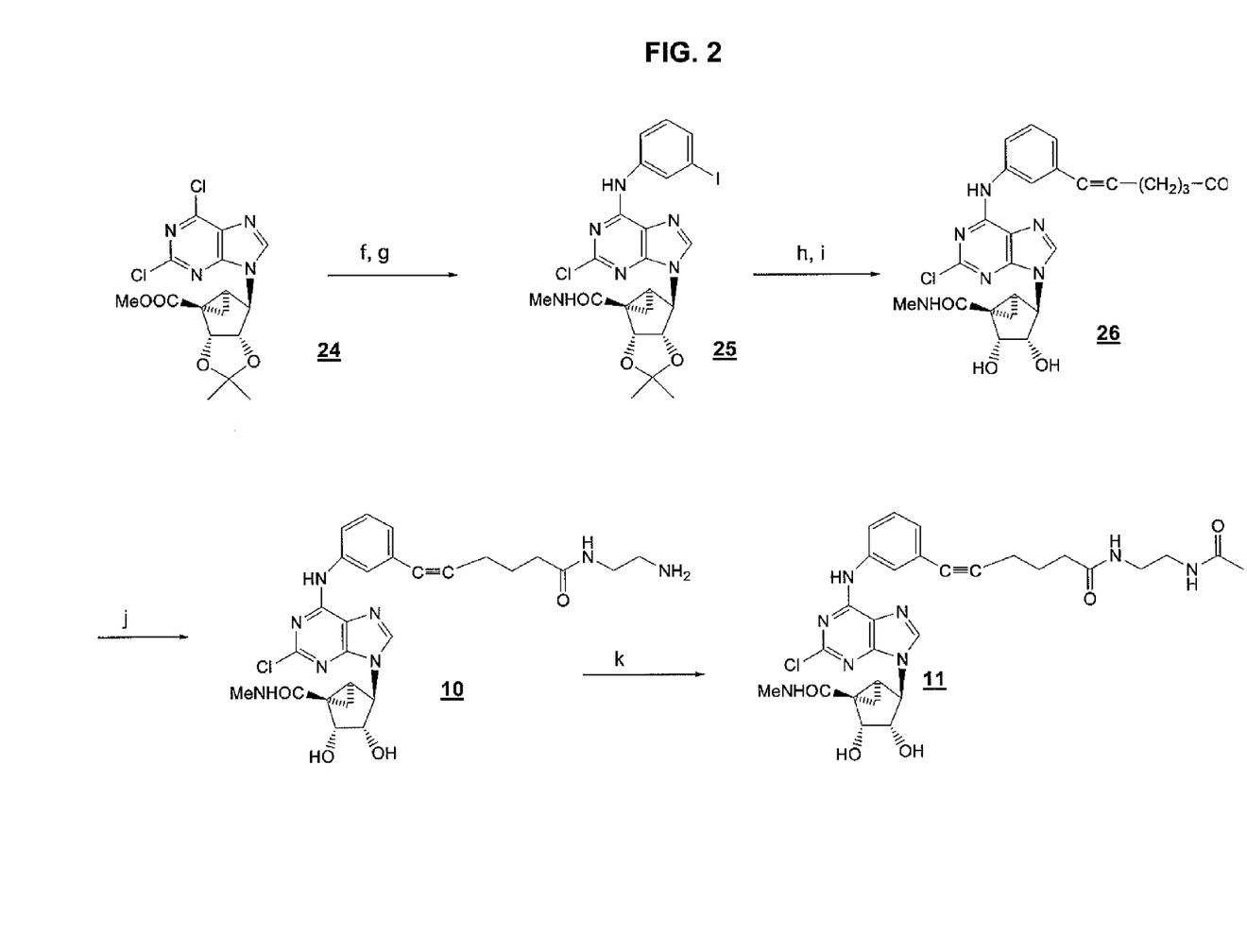
FIG. 2 depicts a reaction scheme for the synthesis of compounds 26, 10, and 11 in accordance with an embodiment of the invention. Reagents and conditions: (f) 3-iodobenzylamine; (g) $MeNH_2$, EtOH; (h) $HC{\equiv}C(CH_2)_3COOCH_3$, CuI, DMF, $Et_3N$; (i) TFA, MeOH, $H_2O$; (j) $H_2NCH_2CH_2NH_2$; (k) $Ac_2O$.
Figure 3:
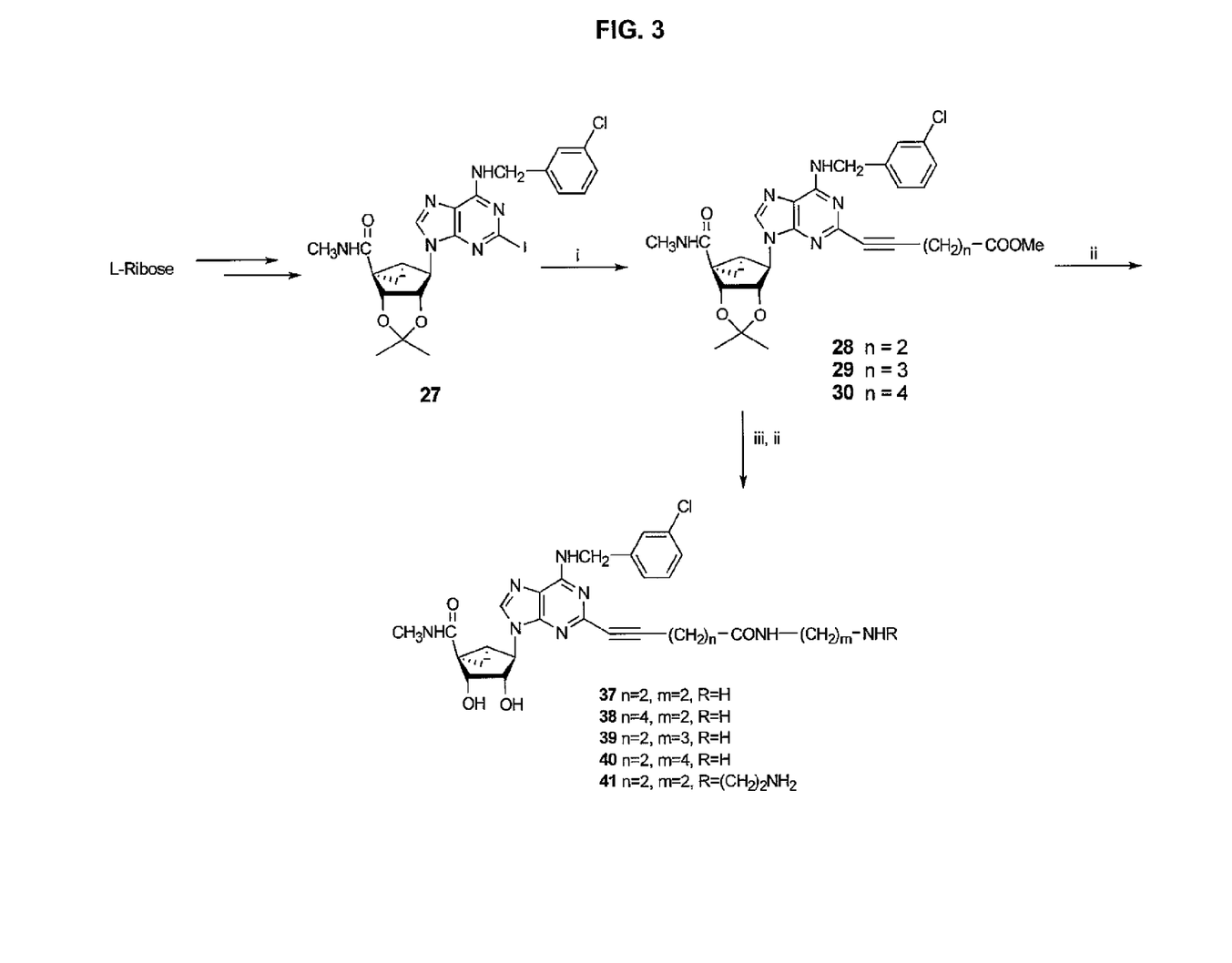
FIG. 3 depicts a reaction scheme for the synthesis of compounds 37 to 41 in accordance with an embodiment of the invention.

(1'S,2'R,3'S,4'S,5'S)-4'-[6-(3-Chlorobenzylamino)-2-(4-methoxycarbonyl-1-butynyl)-9-yl]-2',3'-O-isopropylidenebicyclo[3.1.0]hexane-1'-carboxylic acid N-methylamide (28) (FIG. 3). To a solution of compound 27 (52 mg, 0.087 mmol) in anhydrous DMF (1.5 mL), PdCl$_2$(PPh$_3$)$_2$ (12 mg, 0.017 mmol), CuI (2 mg, 0.010 mmol), methyl-co-pentynate (39 mg, 0.347 mmol) and then triethylamine (0.12 mL, 0.86 mmol) was added. The reaction mixture was stirred at room temperature for overnight. Solvent was evaporated under vacuum, and the residue was purified on flash silica gel column chromatography (CH$_2$Cl$_2$:MeOH=30:1) to give compound 28 (40 mg, 78%) as foamy syrup. $^1$H NMR (CD$_3$OD, 300 MHz) δ 8.16 (s, 1H), 7.42-7.44 (m, 4H), 5.81 (d, J=6.7 Hz, 1H), 5.02 (s, 1H), 4.82 (m, 2H) 3.78 (s, 3H), 2.85 (s, 3H), 2.72-281 (m, 5H), 2.09-2.14 (m, 1H), 1.55 (s, 3H), 1.41 (t, J=5.1 Hz, 1H), 1.29 (s, 3H), 0.82-0.96 (m, 1H). HRMS calculated for C$_{29}$H$_{32}$ClN$_6$O$_5$ (M+H)$^+$: 579.2105; found 579.2123.

(1'S,2'R,3'S,4'S,5'S)-4'-[6-(3-Chlorobenzylamino)-2-(6-methoxycarbonyl-1-hexynyl)-9-yl]-2',3'-O-isopropylidenebicyclo[3.1.0]hexane-1'-carboxylic acid N-methylamide (30). Compound 30 (74%) was synthesized from 27 following the same procedure as for compound 28. $^1$H NMR (CD$_3$OD, 300 MHz) δ 8.12 (s, 1H), 7.41-7.20 (m, 4H), 5.75 (d, J=6.9 Hz, 1H), 4.98 (s, 1H), 4.86 (m, 211), 3.66 (s, 3H), 2.84 (s, 3H), 2.38-2.55 (m, 4H), 2.06-2.15 (m, 1H), 1.64-1.91 (m, 4H), 1.53 (s, 3H), 1.38 (m, 1H), 1.24-1.32 (m, 4H), 0.84-0.97 (m, 1H). HRMS calculated for C$_{31}$H$_{36}$ClN$_6$O$_5$ (M+H)$^+$: 607.2426; found 607.2436.

(1'S, 2'R, 3'S, 4'S, 5'S)-4'-[6-(3-Chlorobenzylamino)-2-(4-(β-aminoethylaminocarbonyl)-1-butynyl)-9-yl]-2',3'-dihydroxybicyclo[3.1.0]hexane-1'-carboxylic acid N-methylamide (37). To a solution of compound 28 (20 mg. 0.034 mmol) in methanol (0.3 mL), ethylenediamine (1.5 mL) was added and stirred for overnight at room temperature. Solvent was evaporated and the residue was roughly purified on flash silica gel column chromatography. The aminated product was dissolved in methanol (1.5 mL) and 10% trifluoroacetic acid (1.5 mL) and heated at 70° C. for 15 h. Solvent was evaporated and the residue was purified on flash silica gel column chromatography (CH$_2$Cl$_2$:MeOH:NH$_4$OH=10:1:0.1) to give compound 37 (15 mg, 79%). $^1$H NMR (CD$_3$OD, 300 MHz) δ 8.09 (s, 1H), 7.39 (s, 1H), 7.27-7.32 (m, 3H), 4.99 (d, J=6.6 Hz, 1H), 4.78-4.91 (m, 2H), 3.97 (d, J=6.6 Hz, 1H), 3.33-3.36 (m, 4H), 2.87 (s, 3H), 2.75-2.80 (m, 4H), 2.53 (t, 7.2 Hz, 2H), 2.59-3.41 (m, 1H), 1.88 (t, J=4.5 Hz, 1H), 1.34-1.43 (m, 1H). HRMS calculated for C$_{27}$H$_{31}$ClN$_6$O$_2$Na (M+Na)$^+$: 589.2068; found 589.2054.

(1'S,2'R,3'S,4'S,5'S)-4'-[6-(3-Chlorobenzylamino)-2-(6-(β-aminoethylaminocarbonyl)-1-hexynyl)-9-yl]-2',3'-dihydroxybicyclo[3.1.0]hexane-1'-carboxylic acid N-methylamide (38). Compound 38 (82%) was synthesized from compound 30 following the same procedure as for compound 37. NMR (CD$_3$OD, 300 MHz) δ 8.06 (s, 1H), 7.40 (s, 1H), 7.28-7.31 (m, 3H), 5.01 (d, J=6.7 Hz, 1H), 4.84 (m, 2H), 3.98 (d, J=6.7 Hz, 1H), 3.24 (t, J=6.3 Hz, 2H), 2.85 (s, 3H), 2.72 (t, J=6.3 Hz, 2H), 2.48 (t, J=6.2 Hz, 2H), 2.27 (t, J=7.5 Hz, 2H), 2.23 (m, 1H), 1.74-1.88 (m, 3H), 1.60-1.73 (m, 2H), 1.32-1.42 (m, 1H), 0.81-0.98 (m, 1H). HRMS calculated for C$_{29}$H$_{36}$ClN$_8$O$_4$ (M+H)$^+$: 595.2527; found 595.2548.

(1'S, 2'R, 3'S, 4'S, 5'S)-4'[6-(3-Chlorobenzylamino)-2-4-(β-aminopropylaminocarbonyl)-1-butynyl)-9-yl]-2',3'-dihydroxybicyclo[3.1.0]hexane-1'-carboxylic acid N-methylamide (39). Compound 39 (78%) was synthesized from compound 28 following the same procedure as for compound 37. $^1$H NMR (CD$_3$OD, 300 MHz) δ 8.09 (s, 1H), 7.39 (s, 1H), 7.25-7.32 (m, 3H), 5.03 (d. J=6.6 Hz, 1H), 4.81-4.86 (m, 2H), 4.99 (d. J=6.6 Hz, 1H), 3.35-3.37 (m, 2H), 2.87 (s, 3H), 2.67-2.82 (m, 4H), 2.52 (t, J=6.9 Hz, 2H), 2.06-2.10 (m, 1H), 1.85 (t, J=3.6 Hz, 1H), 1.62-1.71 (m, 2H), 1.36-1.40 (m, 1H), 0.78-0.92 (m, 1H). HRMS calculated for C$_{28}$H$_{34}$ClN$_8$O$_4$ (M+H)$^+$: 581.2392; found 581.2376.

(1'S, 2'R, 3'S, 4'S, 5'S)-4'-[6-(3-Chlorobenzylamino)-2-(4-(β-aminobutylaminocarbonyl)-1-butynyl)-9-yl]-2',3'-dihydroxybicyclo[3.1.0]hexane-1'-carboxylic acid N-methylamide (40). Compound 40 (74%) was synthesized from compound 28 following the same procedure as for compound 37. $^1$H NMR (CD$_3$OD, 300 MHz) δ 8.09 (s, 1H), 7.40 (s, 1H), 7.28-7.32 (m, 3H), 5.04 (d, J=5.9 Hz, 1H), 4.82-4.86 (m, 2H), 3.99 (d, J=6.0 Hz, 1H), 3.34-3.38 (m, 2H), 2.87 (s, 3H), 2.69-2.82 (m, 4H), 248-2.54 (m, 2H), 2.06-2.10 (m, 1H), 1.86 (t, J=5.1 Hz, 1H), 1.52-1.56 (m, 4H), 1.36-1.41 (m, 1H), 0.76-0.97 (m, 1H). HRMS calculated for C$_{29}$H$_{36}$ClN$_8$O$_4$ (M+H)$^+$: 595.2548; found 595.2533.

(1'S,2'R,3'S,4'S,5'S)-4'-[6-(3-Chlorobenzylamino)-2-(4-(β-aminoethyl-N-aminoethylaminocarbonyl)-1-butanyl)-9-yl]-2',3'-dihydroxybicyclo[3.1.0]hexane-1'-carboxylic acid N-methylamide (41). Compound 41 (69%) was synthesized from compound 28 following the same procedure as for compound 37. $^1$H NMR (CD$_3$OD, 300 MHz) δ 8.10 (s, 1H), 7.40 (s, 1H), 7.25-7.33 (m, 3H), 5.05 (d, J=5.4 Hz, 1H), 4.78-4.86 (m, 2H), 4.01 (d, J=6.3 Hz, 1H), 3.33-3.36 (m, 2H), 2.87 (s, 3H), 2.73-2.86 (m, 6H), 2.58 (t, J=6.9 Hz, 2H), 2.06-2.10 (m, 1H), 1.86 (t, J=5.1 Hz, 1H), 1.36-1.41 (m, 1H), 0.88-0.94 (m, 1H). HRMS calculated for C$_{29}$H$_{37}$ClN$_9$O$_4$ (M+H)$^+$: 610.2657; found 610.2676.

(1'S,2'R,3'S,4'S,5'S)-4'-[6-(3-Chlorobenzylamino)-2-(4-methoxycarbonyl)-1-butynyl)-9-yl]-2',3'-dihydroxybicyclo[3.1.0]hexane-1'-carboxylic acid N-methylamide (35). A solution of compound 28 (67 mg, 0.115 mmol) in methanol (3 mL) and 10% trifluoromethanesulfonic acid (2 mL) was heated at 70° C. for overnight. Solvent was evaporated and the residue was purified on flash silica gel column chromatography (CH$_2$Cl$_2$:MeOH=20:1) to give compound 35 (46 mg, 75%). $^1$H NMR (CD$_3$OD, 300 MHz) δ 8.13 (s, 1H), 7.40 (s, 1H), 7.22-7.45 (m, 3H), 5.10 (d, J=6.3 Hz, 1H), 4.80-4.86 (m, 2H), 4.03 (d, J=6.6 Hz, 1H), 3.63 (s, 3H), 2.86 (s, 3H), 2.76-2.85 (m, 2H), 2.46-2.58 (m, 2H), 2.05-2.10 (m, 1H), 1.77-1.83 (m, 1H), 1.35-1.40 (m, 1H), 0.82-0.96 (m, 1H). HRMS calculated for C$_{26}$H$_{28}$ClN$_6$O$_5$ (M+H)$^+$: 539.1731; found 539.1743.

(1'S,2'R,3'S,4'S,5'S)-4'-[6-(3-Chlorobenzylamino)-2-(6-methoxycarbonyl)-1-hexynyl)-9-yl]-2',3'-dihydroxybicyclo[3.1.0]hexane-1'-carboxylic acid N-methylamide (36). Compound 36 (71%) was synthesized from compound 30 following the same procedure as for compound 35. $^1$H NMR (CD$_3$OD, 300 MHz) δ 8.11 (s, 1H), 7.43 (s, 1H), 7.24-7.45 (m, 3H), 5.02 (d, J=6.3 Hz, 1H), 4.80-4.86 (m, 2H), 3.99 (d, J=6.6 Hz, 1H), 3.67 (s, 3H), 2.87 (s, 3H), 2.51 (t, J=6.9 Hz, 2H), 2.42 (t, J=7.5 Hz, 2H), 2.07-2.1 (m, 1H), 1.66-1.88 (m, 4H), 1.35-1.40 (m, 2H), 0.98-1.21 (m, 1H). HRMS calculated for C$_{28}$H$_{32}$ClN$_6$O$_5$ (M+H)$^+$: 567.2123; found 567.2114.

(1'S,2'R,3'S,4'S,5SS)-4'-[6-(3-Chlorobenzylamino)-2-(4-hydroxycarbonyl)-1-butynyl)-9-yl]-2',3'-dihydroxybicyclo[3.1.0]hexane-1'-carboxylic acid N-methylamide (33). To a solution of ester 35 (30 mg, 0.055 mmol) in methanol (1.5 mL), 1M solution of potassium hydroxide (1 mL) was added and stirred at room temperature for overnight. The reaction mixture was neutralized with acetic acid and solvent was evaporated and the residue was purified on flash silica gel column chromatography (CH$_2$Cl$_2$:MeOH=10:1) to give compound 33 (23 mg, 80%). $^1$H NMR (CD$_3$OD, 300 MHz) δ 8.06 (s, 1H), 7.38 (s, 1H), 7.24-7.35 (m, 3H), 5.14 (d, J=5.8 Hz, 1H), 4.79-4.86 (m, 2H), 4.03 (d, J=6.3 Hz, 1H), 2.87 (s, 3H), 2.42-2.80 (m, 4H), 2.04-2.32 (m, 1H), 1.82 (t, J=4.8 Hz, 1H), 1.36-1.40 (m, 1H), 0.84-0.97 (m, 1H). HRMS calculated for C$_{25}$H$_{26}$ClN$_6$O$_5$ (M+H)$^+$: 525.9562; found 525.9583.

(1'S,2'R,3'S,4'S,5SS)-4'-[6-(3-Chlorobenzylamino)-2-(4-hydroxycarbonyl)-1-hexynyl)-9-yl]-2',3'-dihydroxybicyclo[3.1.0]hexane-1'-carboxylic acid N-methylamide (34). Compound 34 (77%) was prepared from compound 35 following the same method as for compound 33. $^1$H NMR (CD$_3$OD, 300 MHz) δ 8.08 (s, 1H), 7.43 (s, 1H), 7.24-7.42 (m, 3H), 5.06 (d, J=6.6 Hz, 1H), 4.81-4.85 (m, 2H), 4.02 (d, J=6.0 Hz, 1H), 2.87 (s, 3H), 2.50 (t, J=6.9 Hz, 2H), 2.35 (t, J=7.5 Hz, 2H), 2.12-2.04 (m, 1H), 1.70-1.87 (m, 4H), 1.35-1.40 (m, 2H), 0.84-0.96 (m, 1H). HRMS calculated for C$_{27}$H$_{30}$ClN$_6$O$_5$ (M+H)$^+$: 553.1966; found 553.1976.

(1'S,2'R,3'S,4'S,5'S)-4'-[6-(3-Chlorobenzylamino)-2-(N-biotinyl(β-aminoethylaminocarbonyl)-1-butynyl)-9-yl]-2',3'-dihydroxybicyclo[3.1.0]hexane-1'-carboxylic acid N-methylamide (42). To a solution of compound 37 (4 mg, 0.007 mmol) in dry DMF (0.5 mL), biotin (1.89 mg, 0.0077 mmol), HATU (3.2 mg, 0.0084 mmol) and DIEA (1.6 µL, 0.009 mmol) was added and stirred at room temperature for overnight. Solvent was evaporated and the residue was purified on flash silica gel column chromatography (CH$_2$Cl$_2$:MeOH:NH$_4$OH=5:1:0.1) to give compound 42 (3.5 mg, 62%). $^1$H NMR (CD$_3$OD, 300 MHz) δ 8.14 (s, 1H), 7.43 (s, 1H), 7.29-7.39 (m, 3H), 5.07 (d, J=6.9 Hz, 1H), 4.78-4.86 (m, 2H), 4.48-4.52 (m, 1H), 4.28-4.32 (m, 1H), 4.04 (d, J=6.3 Hz, 1H), 3.70-3.82 (m, 2H), 3.24-3.31 (m, 1H), 3.08-3.23 (m, 1H), 2.91 (s, 3H), 2.70-2.83 (m, 4H), 2.56 (t, J=7.5 Hz, 2H), 2.04-2.15 (m, 2H), 1.89 (t, J=5.1 Hz, 1H), 1.33-1.70 (m, 10H), 0.84-1.02 (m, 1H). HRMS calculated for C$_{37}$H$_{46}$ClN$_{10}$O$_6$S (M+H)$^+$: 793.3011; found 793.3030.

(1'S,2'R,3'S,4'S,5'S)-4'-[6-(3-Chlorobenzylamino)-2-(N-biotinyl{5-aminopentanyl}(β-aminoethylaminocarbonyl)-1-butynyl)-9-yl]-2',3'-dihydroxybicyclo[3.1.0]hexane-1'-carboxylic acid N-methylamide (43). To a solution of compound 37 (3.4 mg, 0.0059 mmol) in DMF (0.5 mL), sulfo-NHS-LC-Biotin (10 mg, 0.017 mmol) and a drop of triethyl amine was added and stirred for overnight at room temperature. Solvent was evaporated and the residue was purified on flash silica gel column chromatography (CH$_2$Cl$_2$: MeOH:NH$_4$OH=7:1:0.1) to give compound 43 (2.9 mg, 55%). %). $^1$H NMR (CD$_3$OD, 300 MHz) δ 7.99 (s, 1H), 7.29 (s, 1H), 7.19-7.32 (m, 3H), 4.93 (d, J=5.4 Hz, 1H), 4.70-4.80 (n, 2H), 4.36-4.42 (m, 1H), 4.16-4.22 (m, 1H), 3.88 (d, J=6.9 Hz, 1H), 3.42-3.62 (m, 2H), 3.03-3.15 (m, 4H), 2.89 (s, 3H), 2.56-2.86 (m, 6H), 2.41 (t, J=6.6 Hz, 1H), 1.96-2.13 (m, 5H), 1.15-1.16 (m, 14H), 0.74-0.88 (m, 1H). C$_{43}$H$_{57}$ClN$_{11}$O$_7$S (M+H)$^+$: 906.3852; found 906.3878.

(1'S,2'R,3'S,4'S,5'S)-4'-[6-(3-Chlorobenzylamino)-2-(N-Cyanine(β-aminoethylaminocarbonyl)-1-butynyl)-9-yl]-2',3'-dihydroxybicyclo[3.1.0]hexane-1'-carboxylic acid N-methylamide (44). To a solution of compound 37 (1.69 mg, 0.0029 mmol) in DMF (0.3 mL), Cy5 fluorescent dye (2.36 mg, 0.0029 mmol) and bicarbonate buffer (60 μL) was added and stirred at room temperature for overnight. The reaction mixture was covered with aluminum foil in order to protect from light. Solvent was evaporated and the residue was purified on flash silica gel column chromatography (CH$_2$Cl$_2$: MeOH:NH$_4$OH=3:1:0.1) to give compound 44 (3.2 mg, 89%) as a dark blue syrup. $^1$H NMR (CD$_3$OD, 300 MHz) δ 8.21-8.42 (m, 1H), 8.08 (s, 1H), 7.85-7.93 (m, 2H), 7.29-7.46 (m, 6H), 6.28-6.45 (m, 1H), 5.07 (d, J=6.9 Hz, 1H), 4.84-4.86 (m, 2H), 3.97-4.20 (m, 3H), 3.53 (t, J=6.0 Hz, 2H), 3.12 (t, J=6.0 Hz, 2H), 2.89 (s, 3H), 2.49 (t, J=7.5 Hz, 2H), 2.52-2.64 (m, 2H), 2.01-2.17 (m, 2H), 1.56-1.89 (m, 9H), 1.22-1.49 (m, 10H), 0.86-0.96 (m, 1H).

HRMS calculated for C$_{60}$H$_{68}$ClN$_{10}$O$_{11}$S$_2$ (M$^+$): 1203.4199; found 1203.4175.

Example 2

This example illustrates some of the biological properties of compounds in accordance with an embodiment of the invention.

[$^{125}$I]N$^6$-(4-amino-3-iodo-benzyl)adenosine-5'-N-methyluronamide ([$^{125}$I]I-AB-MECA; 2000 Ci/mmol), [$^3$H]R-PIA (R—N$^6$-[phenylisopropyl]adenosine, 34 Ci/mmol), [$^3$H]CGS21680 (2-[p-(2-carboxyethyl)phenylethylamino]-5'-N-ethylcarboxamido-adenosine, 47 Ci/mmol) and [$^3$H]cAMP (40 Ci/mmol) were from Amersham Pharmacia Biotech (Buckinghamshire, UK). NECA, CGS21680, CPA, and R-PIA were purchased from Sigma-RBI (St. Louis, Mo.). Other chemicals were from standard commercial sources and of analytical grade.

CHO cells stably expressing human recombinant ARs were cultured in DMEM and F12 (1:1) supplemented with 10% fetal bovine serum, 100 units/ml penicillin, 100 μg/mL streptomycin, 2 μmol/ml glutamine and 800 μg/ml geneticin. After harvest and homogenization, cells were centrifuged at 500 g for 10 min, and the pellet was re-suspended in 50 mM Tris.HCl buffer (pH 7.4) containing 10 mM MgCl$_2$, 1 mM EDTA. The suspension was homogenized with an electric homogenizer for 10 sec, and was then re-centrifuged at 20,000 g for 20 min at 4° C. The resultant pellets were resuspended in buffer in the presence of 3 Units/ml adenosine deaminase, and the suspension was stored at –80° C. until the binding experiments. The protein concentration was measured as described in Bradford, M. M. et al., *Anal. Biochem*, 1976, 72, 248. For A$_3$AR binding assays, each tube contained 100 μl of membrane suspension, 50 μl of [$^{125}$I]I-AB-MECA (final concentration 0.5 nM), and 50 μl of increasing concentrations of compounds in Tris.HCl buffer (50 mM, pH 7.4) containing 10 mM MgCl$_2$. Nonspecific binding was determined using 10 μM NECA. The mixtures were incubated at 25° C. for 60 min. Binding reactions were terminated by filtration through WHATMAN™ GF/B filters under reduced pressure using a MT-24 cell harvester (Brandell, Gaithersburg, Md.). Filters were washed three times with ice-cold buffer. Radioactivity was determined in a Beckman 5500γ-counter. The binding of [$^3$H]R-PIA to A$_1$ARs and the binding of [$^3$H]CGS21680 to A$_{2A}$ARs were as previously described.[10] Similar competition binding assays were conducted using HEK 293 cell membranes expressing mouse ARs using [$^{125}$I]I-AB-MECA to label A$_1$ or A$_3$ARs and [$^3$H]CGS 21680 to label A$_{2A}$ARs as described in Kreckler L M et al., *J Pharmacol, Exp. Ther.* 2006, 317, 172. IC$_{50}$ values were converted to K$_i$ values as described in Cheng Y-C and Prusoff W H., *Biochem. Pharmacol.* 1973, 22, 3099. Data were expressed as mean±standard error and set forth in Table 1.

TABLE 1

Affinity of a series of (N)-methanocarba adenosine derivatives at three subtypes of ARs in various species.

| Cmpd. | R$^1$ | R$^2$ | Species | A$_1$[a] K$_i$, nM | A$_2$A[a] K$_i$, nM (or % inhib.) | A3[a] K$_i$, nM | Selectivity A$_1$/A$_3$ |
|---|---|---|---|---|---|---|---|
| 1 | 3-chlorobenzyl | I | M | 210 ± 34.4 | (40%)[i] | 1.18 ± 0.11 | 178 |
|   |   |   | H[c] | 2200 | >10000 | 3.6 | 610 |
|   |   |   | R[c] | ND | ND | 3.9 | — |
| 2 | 2,5-dimethoxybenzyl | I | M | 293 ± 29 | (14%)[i] | 1.51 ± 0.36 | 194 |
|   |   |   | H | 3070 ± 820 | (35%)[f] | 1.30 ± 0.27 | 2360 |

TABLE 1-continued

Affinity of a series of (N)-methanocarba adenosine derivatives at three subtypes of ARs in various species.

| Cmpd. | R[1] | R[2] | Species | A$_1$[a] K$_i$, nM | A$_2$A[a] K$_i$, nM (or % inhib.) | A3[a] K$_i$, nM | Selectivity A$_1$/A$_3$ |
|---|---|---|---|---|---|---|---|
| 3 | 3-chlorobenzyl | ethynyl | M | 45.6 ± 7.9 | (41%)[i] | 0.85 ± 0.08 | 53.6 |
|  |  |  | H | 174 ± 23 | (48%)[f] | 1.30 ± 0.38 | 134 |
| 4 | 3-chlorobenzyl | 2-trimethylsilyl-ethynyl | M | 159 ± 22 | (20%)[i] | 4.46 ± 0.57 | 35.6 |
|  |  |  | H | 160 ± 40 | (52%)[f] | 0.98 ± 0.14 | 160 |
| 5 | 3-chlorobenzyl | 1-pentynyl | M | 1390 ± 430 | (42%)[i] | 6.06 ± 1.21 | 229 |
|  |  |  | H | 1040 ± 83 | (80%)[f] | 0.82 ± 0.20 | 1300 |
| 6 | 3-chlorobenzyl | 5-carbomethoxy-1-pentynyl | M | 1340 ± 330 | (50%)[i] | 4.65 ± 0.53 | 288 |
|  |  |  | H | 482 ± 23 | (49%)[f] | 1.17 ± 0.27 | 412 |
| 7 | 3-chlorobenzyl | 5-carboxy-1-pentynyl | M | 10500 ± 1900 | (8%)[i] | 24.4 ± 3.1 | 431 |
|  |  |  | H | 14900 ± 3500 | (43%)[f] | 2.38 ± 0.56 | 6260 |
| 8 | 3-chlorobenzyl | 5-(2-aminoethyl)aminocarbonyl-1-pentynyl | M | 546 ± 62 | (31%)[i] | 8.60 ± 1.02 | 64 |
|  |  |  | H | 454 ± 44 | (81%)[f] | 2.17 ± 0.51 | 209 |
| 9 | 3-(5-carboxy-1-pentynyl)benzyl | Cl | M | 703 ± 71 | (5%)[i] | 14.4 ± 2.5 | 49 |
|  |  |  | H | 320 ± 31 | (14%)[f] | 17.1 ± 1.2 | 19 |
| 10 | 3-(5-(2-aminoethyl)aminocarbonyl-1-pentynyl)benzyl | Cl | M | 151 ± 18 | (39%)[i] | 11.9 ± 2.4 | 13 |
|  |  |  | H | 271 ± 23 | (58%)[f] | 5.21 ± 0.91 | 52 |
| 11 | 3-(5-(2-acetamido-ethy)paminocarbonyl-1-pentynyl)benzyl | Cl | M | 45.4 ± 3.4 | (68%)[i] | 4.65 ± 0.22 | 9.8 |
|  |  |  | H | 181 ± 22 | (80%)f | 2.88 ± 0.54 | 63 |
| 12 | Methyl | Cl | M | 55.3 ± 6.0 | 20400 ± 3200 | 49.0 ± 3.9 | 1.1 |
|  |  |  | H | 2011 ± 1700 | (6%)[d,f] | 2.2 ± 0.6 | 950 |
|  |  |  | R[d,g] | 805[g] | >10,000 | 160 ± 30 | 5.0 |
| 13 | 3-Chlorobenzyl | Cl | M | 15.3 ± 5.8 | 10400 ± 1700 | 1.49 ± 0.46 | 10.3 |
|  |  |  | H[c,d] | 260 ± 60 | 2300 ± 200 | 0.29 ± 0.04 | 900 |
|  |  |  | R[d] | ND | ND | 1.0 |  |
| 14 | 3-Bromobenzyl | Cl | M | 8.79 ± 0.12 | 6390 ± 870 | 0.90 ± 0.22 | 9.8 |
|  |  |  | H[c,d] | 270 | 1300 | 0.38 | 710 |
|  |  |  | R[c] | ND | ND | 0.76 | — |
| 15 | 3-Iodobenzyl | Cl | M | 7.32 ± 1.5 | 5350 ± 860 | 0.80 ± 0.14 | 9.2 |
|  |  |  | H[c] | 136 ± 22 | 784 ± 97 | 1.5 ± 0.2 | 100 |
|  |  |  | R | 83.9[g] | 1660[g] | 1.1 | 76 |
| 16 | 3-(3-Hydroxy-1-propynyl)benzyl | Cl | M | 111 ± 22 | (11%)[i] | 1.94 ± 1.1 | 57.2 |
|  |  |  | H[d] | 2600 ± 300 | (56%)[f] | 2.9 ± 0.7 | 900 |
|  |  |  | R[d] | ND | ND | 1.6 ± 0.6 |  |
| 17 | 2,5-Dimethoxybenzyl | Cl | M | 29.0 ± 3.3 | 44700 ± 5700 | 1.72 ± 0.04 | 17 |
|  |  |  | H[c,d] | 1600 | 10000 | 1.4 | 1100 |
|  |  |  | R[d] | ND | ND | 0.87 |  |
| 18 | 2,2-Diphenylethyl | Cl | M | 6.83 ± 1.5 | 1810 ± 581 | 1.67 ± 0.09 | 4.1 |
|  |  |  | H[c,e] | 1300 ± 100 | 1600 ± 100 | 0.69 ± 0.02 | 1900 |
|  |  |  | R[c] | ND | ND | 10 ± 4 |  |
| 19 | Cyclopropylphenyl | Cl | M | 6.60 ± 1.3 | 38200 ± 5300 | 2.79 ± .089 | 2.4 |
|  |  |  | H[c,d] | 770 ± 50 | 4800 ± 200 | 0.78 ± 0.06 | 990 |
| 20 | 3-Chlorobenzyl | SMe | M | 98.9 ± 18.8 | (32%)[i] | 1.19 ± 0.09 | 83 |
|  |  |  | H[c] | 610 | 10000 | 1.5 | 410 |
| 21 | Methoxy | Cl | M | 1160 ± 130 | (2%)[i] | 877 ± 149 | 1.3 |
|  |  |  | H | 265 ± 45 | (2%)[f] | 149 ± 15 | 1.8 |
| 31 | 3-Iodobenzyl | H | H | 700 ± 270 | 6200 ± 100 | 2.4 ± 0.5 | 100[j] |
| 32 | cyclopentyl | Cl | H | 18.3 ± 6.3 | 3250 ± 300 | 3.7 ± 0.9 | 101[j] |
| 33 | 3-Chlorobenzyl | C≡C(CH$_2$)$_2$COOH | H | (17 ± 3%) | (24 ± 12%) | 61.1 ± 35.8 | 106.2 ± 17.7[j] |
| 34 | 3-Chlorobenzyl | C≡C(CH$_2$)$_4$COOH | H | (5 ± 3%) | (38 ± 2%) | 12.4 ± 1.8 | ND |
| 35 | 3-Chlorobenzyl | C≡C(CH$_2$)$_2$COOCH$_3$ | H | (19 ± 3%) | (43 ± 5%) | 5.5 ± 0.3 | 74.4 ± 5.1[j] |
| 36 | 3-Chlorobenzyl | C≡C(CH$_2$)$_4$COOCH$_3$ | H | (21 ± 8%) | 3540 ± 1370 | 11.1 ± 2.3 | 90.0 ± 6.2[j] |
| 37 | 3-Chlorobenzyl | C≡C(CH$_2$)$_2$CONH(CH$_2$)$_2$NH$_2$ | H | (25 ± 12%) | 550 ± 83 | 2.5 ± 0.5 | ND |

TABLE 1-continued

Affinity of a series of (N)-methanocarba adenosine derivatives at three subtypes of ARs in various species.

| Cmpd. | R¹ | R² | Species | $A_1{}^a$ $K_i$, nM | $A_{2A}{}^a$ $K_i$, nM (or % inhib.) | $A_3{}^a$ $K_i$, nM | Selectivity $A_1/A_3$ |
|---|---|---|---|---|---|---|---|
| 38 | 3-Chlorobenzyl | C≡C(CH₂)₄CONH(CH₂)₂NH₂ | H | (21 ± 6%) | 277 ± 33 | 3.4 ± 0.7 | 100.0 ± 2.4[j] |
| 39 | 3-Chlorobenzyl | C≡C(CH₂)₂CONH(CH₂)₃NH₂ | H | (16 ± 4%) | 979 ± 181 | 3.1 ± 0.4 | 97.9 ± 18.4[j] |
| 40 | 3-Chlorobenzyl | C≡C(CH₂)₂CONH(CH₂)₄NH₂ | H | (30 ± 7%) | 766 ± 109 | 2.1 ± 0.4 | 102.1 ± 13.0[j] |
| 41 | 3-Chlorobenzyl | C≡C(CH₂)₂CO[NH(CH₂)₂]₂NH₂ | H | (14 ± 8%) | 890 ± 110 | 15.4 ± 4.4 | 87.6 ± 21.2[j] |
| 42 | 3-Chlorobenzyl | C≡C(CH₂)₂CONH(CH₂)₂NH-biotin | H | (13 ± 6%) | (51 ± 2%) | 36.4 ± 5.6 | 84.5 ± 12.0[j] |
| 43 | 3-Chlorobenzyl | C≡C(CH₂)₂CONH(CH₂)₂NH-CO(CH₂)₅NH-biotin | H | (8 ± 4%) | (47 ± 11%) | 57.7 ± 16.2 | 106.5 ± 17.7[j] |
| 44 | 3-Chlorobenzyl | C≡C(CH₂)₂CONH(CH₂)₂NH-CO—(CH₂)₅Cy5 | H | (10 ± 4%) | 4730 ± 1020 | 17.2 ± 3.1 | 94.4 ± 9.6[i] | a) Competition radioligand binding assays using [¹²⁵I]N⁶-(4-amino-3-iodobenzyl)adenosine-5'-N-methyl-uronamide (A₁ and A₃ARs) and [³H]2-[p-(2-carboxyethyl)phenyl-ethylamino]-5'-N-ethylcarboxamidoadenosine (A₂ₐAR) were conducted with membranes prepared from HEK293 cells expressing recombinant mouse A₁, A₂ₐ, or A₃ARs. At rat and human ARs, the A₁ radioligand was either [³H]R-phenylisopropyladenosine or [³H]2-chloro-N⁶-cyclopentyladenosine. Values are expressed as the mean ± SEM. ND, not determined.
b) Data from Ge et al. (J. Pharmacol. Exp. Ther., 2006, 319, 1200).
c) EC₅₀ value in activation of the A₂ᵦAR is ≥ 10 μM.
d) Data from Tchilibon et al. (J. Med. Chem., 2005, 48, 1745).
e) Data from Kim et al. (J. Med. Chem., 1994, 37, 3614).
f) Percent Inhibition at 10 μM.
g) Data from Lee et al. (Bioorg. Med. Chem. Lett., 2001, 11, 1333).
i) Percent Inhibition at 100 μM.
j) %Efficacy at the human A₃ AR was determined by inhibition of forskolin-stimulated cyclic AMP production in AR transfected CHO cells.
Data are at 10 μM in comparison to the maximal effect of a full agonist (5'-N-ethylcarboxamidoadenosine) at 100%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of Formula I:

wherein:
R$^1$ is selected from the group consisting of C$_1$-C$_6$ alkyl, C$_1$-C$_6$ alkoxy, hydroxyl, C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ diaryl C$_1$-C$_6$ alkyl, C$_6$-C$_{14}$ aryl C$_1$-C$_6$ alkoxy, heterocyclyl C$_1$-C$_6$ alkyl, heterocyclyl, 4-[[[4-[[[(2-amino C$_1$-C$_6$ alkyl)amino]-carbonyl]-C$_1$-C$_6$ alkyl]anilino]carbonyl]C$_1$-C$_6$ alkyl]C$_6$-C$_{14}$ aryl, and C$_6$-C$_{14}$ aryl C$_3$-C$_8$ cycloalkyl, wherein the aryl or heterocyclyl portion of R$^1$ is optionally substituted with one or more substituents selected from the group consisting of halo, amino, hydroxyl, carboxy, alkoxycarbonyl, aminocarbonyl, alkylaminocarbonyl, dialkylaminocarbonyl, C$_1$-C$_6$ alkyl, C$_2$-C$_6$ alkenyl, C$_2$-C$_6$ alkynyl, C$_1$-C$_6$ alkoxy, C$_6$-C$_{14}$ aryloxy, hydroxy C$_1$-C$_6$ alkyl, hydroxy C$_2$-C$_6$ alkenyl, hydroxy C$_2$-C$_6$ alkynyl, carboxy C$_1$-C$_6$ alkyl, carboxy C$_2$-C$_6$ alkenyl, carboxy C$_2$-C$_6$ alkynyl, aminocarbonyl C$_1$-C$_6$ alkyl, aminocarbonyl C$_2$-C$_6$ alkenyl, aminocarbonyl C$_2$-C$_6$ alkynyl, and any combination thereof; and the alkyl or cycloalkyl portion of R$^1$ is optionally substituted with one or more substituents selected from the group consisting of halo, amino, alkyl, alkoxy, aryloxy, hydroxyalkyl, hydroxyalkenyl, hydroxyalkynyl, aminocarbonylalkoxy, and arylalkoxy, and any combination thereof; or R$^1$ is 7-norbornyl;

R$^2$ is selected from the group consisting of C$_7$-C$_{12}$ cycloalkyl C$_1$-C$_{20}$ alkyl, C$_7$-C$_{12}$ bicycloalkyl C$_1$-C$_{20}$ alkyl, C$_7$-C$_{12}$ bicycloalkenyl C$_1$-C$_{20}$ alkyl, C$_6$-C$_{14}$ aryl C$_1$-C$_{20}$ alkyl, C$_2$-C$_{20}$ alkenyl, C$_7$-C$_{12}$ cycloalkyl C$_2$-C$_{20}$ alkenyl, C$_7$-C$_{12}$ bicycloalkyl C$_2$-C$_{20}$ alkenyl, C$_7$-C$_{12}$ bicycloalkenyl C$_2$-C$_{20}$ alkenyl, C$_6$-C$_{14}$ aryl C$_2$-C$_{20}$ alkenyl, C$_2$-C$_{20}$ alkynyl, C$_1$-C$_{20}$ alkyl C$_2$-C$_{20}$ alkynyl, C$_7$-C$_{12}$ cycloalkyl C$_2$-C$_{20}$ alkynyl, C$_7$-C$_{12}$ bicycloalkyl C$_2$-C$_{20}$ alkynyl, C$_7$-C$_{12}$ bicycloalkenyl C$_2$-C$_{20}$ alkynyl, and C$_6$-C$_{14}$ aryl C$_2$-C$_{20}$ alkynyl, and the alkyl, cycloalkyl, or aryl portion of R$^2$ is optionally substituted with one or more substituents selected from the group consisting of halo, hydroxyl, amino, alkylamino, dialkylamino, mercapto, carboxy, alkoxycarbonyl, aminocarbonyl, alkylaminocarbonyl, dialkylaminocarbonyl, aminoalkylaminocarbonyl, trialkylsilyl, and any combination thereof; or R$^2$ is selected from the group consisting of amino (alkylene-NH—)$_n$ alkylaminocarbonyl wherein n is 1 to 6, aminoalkylcarbonylaminoalkylaminocarbonyl, aminoalkylaminocarbonyl whose amino end is linked to a label, dye, or reporter group, amino (alkylene-NH—)$_n$ alkylaminocarbonyl wherein n is 1 to 6 whose amino end is linked to a label, dye, or reporter group, and aminoalkylcarbonylaminoalkylaminocarbonyl whose amino end is linked to a label, dye, or reporter group;

R$^3$ and R$^4$ are independently selected from the group consisting of hydroxyl, amino, mercapto, ureido, C$_1$-C$_6$ alkyl carbonylamino, hydroxy C$_1$-C$_6$ alkyl, and hydrazinyl; and R$^5$ is selected from the group consisting of C$_1$-C$_3$ alkyl aminocarbonyl, di(C$_1$-C$_3$ alkyl)aminocarbonyl, C$_1$-C$_3$ alkylthio C$_1$-C$_3$ alkyl, halo C$_1$-C$_3$ alkyl, hydrazinyl, amino C$_1$-C$_3$ alkyl, C$_3$-C$_6$ cycloalkylamino, hydroxylamino, and C$_2$-C$_3$ alkenyl;

or a pharmaceutically acceptable salt thereof.

2. The compound of claim 1, wherein:
R$^1$ is selected from the group consisting of C$_1$-C$_6$ alkyl, C$_1$-C$_6$ alkoxy, hydroxyl, C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ diaryl C$_1$-C$_6$ alkyl, C$_6$-C$_{14}$ aryl C$_1$-C$_6$ alkoxy, heterocyclyl C$_1$-C$_6$ alkyl, heterocyclyl, 4-[[[4-[[[(2-amino C$_1$-C$_6$ alkyl)amino]-carbonyl]-C$_1$-C$_6$ alkyl]anilino]carbonyl]C$_1$-C$_6$ alkyl]C$_6$-C$_{14}$ aryl, and C$_6$-C$_{14}$ aryl C$_3$-C$_8$ cycloalkyl, wherein the aryl or heterocyclyl portion of R$^1$ is optionally substituted with one or more substituents selected from the group consisting of halo, amino, hydroxyl, carboxy, alkoxycarbonyl, aminocarbonyl, alkylaminocarbonyl, dialkylaminocarbonyl, C$_1$-C$_6$ alkyl, C$_2$-C$_6$ alkenyl, C$_2$-C$_6$ alkynyl, C$_1$-C$_6$ alkoxy, C$_6$-C$_{14}$ aryloxy, hydroxy C$_1$-C$_6$ alkyl, hydroxy C$_2$-C$_6$ alkenyl, hydroxy C$_2$-C$_6$ alkynyl, carboxy C$_1$-C$_6$ alkyl, carboxy C$_2$-C$_6$ alkenyl, carboxy C$_2$-C$_6$ alkynyl, aminocarbonyl C$_1$-C$_6$ alkyl, aminocarbonyl C$_2$-C$_6$ alkenyl, aminocarbonyl C$_2$-C$_6$ alkynyl, and any combination thereof; and the alkyl or cycloalkyl portion of R$^1$ is optionally substituted with one or more substituents selected from the group consisting of halo, amino, alkyl, alkoxy, aryloxy, hydroxyalkyl, hydroxyalkenyl, hydroxyalkynyl, aminocarbonylalkoxy, and arylalkoxy, and any combination thereof; or R$^1$ is 7-norbornyl;

R$^2$ is selected from the group consisting of C$_7$-C$_{12}$ cycloalkyl C$_1$-C$_{20}$ alkyl, C$_7$-C$_{12}$ bicycloalkyl C$_1$-C$_{20}$ alkyl, C$_7$-C$_{12}$ bicycloalkenyl C$_1$-C$_{20}$ alkyl, C$_6$-C$_{14}$ aryl C$_1$-C$_{20}$ alkyl, C$_2$-C$_{20}$ alkenyl, C$_7$-C$_{12}$ cycloalkyl C$_2$-C$_{20}$ alkenyl, C$_7$-C$_{12}$ bicycloalkyl C$_2$-C$_{20}$ alkenyl, C$_7$-C$_{12}$ bicycloalkenyl C$_2$-C$_{20}$ alkenyl, C$_6$-C$_{14}$ aryl C$_2$-C$_{20}$ alkenyl, C$_2$-C$_{20}$ alkynyl, C$_7$-C$_{12}$ cycloalkyl C$_2$-C$_{20}$ alkynyl, C$_7$-C$_{12}$ bicycloalkyl C$_2$-C$_{20}$ alkynyl, C$_7$-C$_{12}$ bicycloalkenyl C$_2$-C$_{20}$ alkynyl, and C$_6$-C$_{14}$ aryl C$_2$-C$_{20}$ alkynyl, and the alkyl, cycloalkyl, or aryl portion of R$^2$ is optionally substituted with one or more substituents selected from the group consisting of halo, hydroxyl, amino, alkylamino, dialkylamino, mercapto, carboxy, alkoxycarbonyl, aminocarbonyl, alkylaminocarbonyl, dialkylaminocarbonyl, aminoalkylaminocarbonyl, trialkylsilyl, and any combination thereof;

R$^3$ and R$^4$ are independently selected from the group consisting of hydroxyl, amino, mercapto, ureido, C$_1$-C$_6$ alkyl carbonylamino, hydroxy C$_1$-C$_6$ alkyl, and hydrazinyl; and R$^5$ is selected from the group consisting of C$_1$-C$_3$ alkyl aminocarbonyl, di(C$_1$-C$_3$ alkyl)aminocarbonyl, C$_1$-C$_3$ alkylthio C$_1$-C$_3$ alkyl, halo C$_1$-C$_3$ alkyl, hydrazinyl, amino C$_1$-C$_3$ alkyl, C$_3$-C$_6$ cycloalkylamino, hydroxylamino, and C$_2$-C$_3$ alkenyl;

or a pharmaceutically acceptable salt thereof.

3. A compound of Formula I:

wherein $R^1$ is selected from the group consisting of $C_1$-$C_6$ alkyl, $C_3$-$C_8$ cycloalkyl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_3$-$C_8$ cycloalkyl, and heterocyclyl $C_1$-$C_6$ alkyl, wherein the aryl or heterocyclyl portion of $R^1$ is optionally substituted with one or more substituents selected from the group consisting of halo, amino, $C_1$-$C_6$ alkyl, alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy, and any combination thereof;

$R^2$ is selected from the group consisting of $C_7$-$C_{12}$, cycloalkyl $C_1$-$C_{20}$ alkyl, $C_2$-$C_{12}$ bicycloalkyl $C_1$-$C_{20}$ alkyl, $C_2$-$C_{12}$ bicycloalkenyl $C_1$-$C_{20}$ alkyl, $C_6$-$C_{12}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, $C_1$-$C_{20}$ alkyl $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, and $C_6$-$C_{14}$ aryl $C_2$-$C_{20}$ alkynyl, and the alkyl, cycloalkyl, or aryl portion of $R^2$ is optionally substituted with one or more substituents selected from the group consisting of halo, hydroxyl, amino, alkylamino, dialkylamino, mercapto, carboxy, alkoxycarbonyl, aminocarbonyl, alkylaminocarbonyl, dialkylaminocarbonyl, aminoalkylaminocarbonyl, trialkylsilyl, and any combination thereof; or $R^2$ is selected from the group consisting of amino (alkylene-NH—)$_B$ alkylaminocarbonyl wherein n is 1 to 6, aminoalkylcarbonylaminoalkylaminocarbonyl, aminoalkylaminocarbonyl whose amino end linked to a label, dye, or reporter group, amino (alkylene-NH—)$_n$ alkylaminocarbonyl wherein n is 1 to 6 whose amino end is linked to a label, dye, or reporter group, and aminoalkylcarbonylaminoalkylaminocarbonyl whose amino end is linked to a label, dye, or reporter group;

$R^3$ and $R^4$ are independently selected from the group consisting of hydroxyl, amino mercapto, ureido, $C_1$-$C_6$ alkyl carbonylamino, hydroxy $C_1$-$C_6$ alkyl, and hydrazinyl; and $R^5$ is selected from the group consisting of $C_1$-$C_3$ alkyl aminocarbonyl, di($C_1$-$C_3$ alkyl)aminocarbonyl, $C_1$-$C_3$ alkylthio $C_1$-$C_3$ alkyl, halo $C_1$-$C_3$ alkyl, hydrazinyl, amino $C_1$-$C_3$ alkyl, $C_3$-$C_{12}$ cycloalkylamino, hydroxylamino, and $C_2$-$C_{12}$ alkenyl;

or a pharmaceutically acceptable salt thereof.

4. The compound of claim 1, wherein $R^1$ is selected from the group consisting of methyl, cyclopentyl, benzyl, diphenyl ethyl, phenyl cyclopropyl, diphenyl cyclopropyl, and 2,2,-diphenylethyl, wherein the phenyl portion of $R^1$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, and any combination thereof, or a pharmaceutically acceptable salt thereof.

5. The compound of claim 1, wherein $R^1$ is benzyl which is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, and any combination thereof, or a pharmaceutically acceptable salt thereof.

6. The compound of claim 1, wherein $R^1$ is benzyl or benzyl substituted with one or more substituents selected from the group consisting of halo, amino, methyl, methoxy, phenoxy, hydroxymethyl, hydroxypropynyl, carboxypropynyl, alkoxycarbonylpropynyl, aminocarbonyl methoxy, and benzyloxy, and any combination thereof, or a pharmaceutically acceptable salt thereof.

7. The compound of claim 1, wherein $R^1$ is methyl, cyclopentyl, or 7-norbornyl, or a pharmaceutically acceptable salt thereof.

8. The compound of claim 1, wherein $R^1$ is selected from the group consisting of 3-chlorobenzyl, 3-bromobenzyl, 3-iodobenzyl, 3-(3-hydroxypropynyl)benzyl, and 2,5-dimethoxybenzyl, or a pharmaceutically acceptable salt thereof.

9. The compound of claim 4, wherein $R^1$ is trans-2-phenyl-1-cyclopropyl or 2,2-diphenylethyl, or a pharmaceutically acceptable salt thereof.

10. The compound of claim 1, wherein $R^2$ is selected from the group consisting of $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, and $C_6$-$C_{14}$ aryl $C_2$-$C_{20}$ alkynyl, or a pharmaceutically acceptable salt thereof.

11. The compound of claim 1, wherein $R^2$ is $C_2$-$C_{20}$ alkynyl, or a pharmaceutically acceptable salt thereof.

12. The compound of claim 1, wherein the alkyl, cycloalkyl, or aryl portion of $R^2$ is substituted with one or more substituents selected from the group consisting of halo, hydroxyl, amino, alkylamino, dialkylamino, mercapto, carboxy, alkoxycarbonyl, aminocarbonyl, alkylaminocarbonyl, dialkylaminocarbonyl, aminoalkylaminocarbonyl, trialkylsilyl, and any combination thereof, or a pharmaceutically acceptable salt thereof.

13. The compound of claim 1, wherein $R^3$ and $R^4$ are independently selected from the group consisting of hydroxyl, amino, mercapto, and ureido, or a pharmaceutically acceptable salt thereof.

14. The compound of claim 1, wherein $R^5$ is selected from the group consisting of $C_1$-$C_3$ alkyl aminocarbonyl, di($C_1$-$C_3$ alkyl)aminocarbonyl, $C_1$-$C_3$ alkylthio $C_1$-$C_3$ alkyl, halo $C_1$-$C_3$ alkyl, amino $C_1$-$C_3$ alkyl, and $C_3$-$C_6$ cycloalkylamino, or a pharmaceutically acceptable salt thereof.

15. The compound of claim 1, wherein $R^1$ is 3-chlorobenzyl, 3-iodobenzyl, or cyclopentyl, $R^2$ is ethynyl, $R^3$ and $R^4$ are hydroxyl, and $R^5$ is methylamino carbonyl, or a pharmaceutically acceptable salt thereof.

16. The compound of claim 1, wherein $R^1$ is 3-chlorobenzyl, $R^2$ is 2-(trimethylsilyl)ethynyl, 1-pentynyl, 5-methoxycarbonyl-1-pentynyl, 5-carboxy-1-pentynyl, or 5-(2-aminoethyl)aminocarbonyl-1-pentynyl, $R^3$ and $R^4$ are hydroxyl, and $R^5$ is methylamino carbonyl, or a pharmaceutically acceptable salt thereof.

17. The compound of claim 1, wherein $R^2$ is selected from the group consisting of carboxyalkylalkynyl, alkoxycarbonylalkylalkynyl, aminoalkylaminocarbonylalkyl alkynyl, amino (alkylene-NH—)$_n$ alkylaminocarbonyl wherein n is 1 to 6, aminoalkylcarbonylaminoalkylaminocarbonyl, aminoalkylaminocarbonyl whose amino end is linked to a label, dye, or reporter group, amino (alkylene-NH—)$_n$ alkylaminocarbonyl wherein n is 1 to 6 whose amino end is linked to a label, dye, or reporter group, aminoalkylcarbonylaminoalkylaminocarbonyl whose amino end is linked to a label, dye, or reporter group.

18. The compound of claim 1, wherein $R^1$ is 3-chlorobenzyl, $R^2$ is selected from the group consisting of C≡C(CH$_2$)$_2$COOH, C≡C(CH$_2$)$_4$COOH, C≡C(CH$_2$)$_2$COOCH$_3$, C≡C(CH$_2$)$_4$COOCH$_3$, C≡C(CH$_2$)$_2$CONH(CH$_2$)$_2$NH$_2$, C≡C(CH$_2$)$_4$CONH(CH$_2$)$_2$NH$_2$, C≡C(CH$_2$)$_2$CONH(CH$_2$)$_3$NH$_2$, C≡C(CH$_2$)$_2$CONH(CH$_2$)$_4$NH$_2$, C≡C(CH$_2$)$_2$CO[NH (CH$_2$)$_2$]$_2$NH$_2$, C≡C(CH$_2$)$_2$CONH(CH$_2$)$_2$NH-biotin, and C≡C(CH$_2$)$_2$CONH(CH$_2$)$_2$NH—CO(CH$_2$)$_5$NH-biotin, and C≡C(CH$_2$)$_2$CONH(CH$_2$)$_2$NH—CO—(CH$_2$)$_5$Cy$_5$ wherein Cy$_5$ is a cyanine dye,
R$^3$ and R$^4$ are hydroxyl, and
R$^5$ is methylamino carbonyl,
or a pharmaceutically acceptable salt thereof.

19. A compound of Formula II:

Formula II wherein:
R$^6$ is C$_6$-C$_{14}$ aryl C$_1$-C$_6$ alkyl wherein the C$_6$-C$_{14}$ aryl is substituted with a group represented by C≡C—(CH$_2$)$_n$—COR$^{11}$ wherein R$^{11}$ is selected from the group consisting of OH, OR$^{12}$, and NR$^{13}$R$^{14}$, wherein R$^{12}$ is selected from the group consisting of C$_1$-C$_6$ alkyl, C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ and diaryl C$_1$-C$_6$ alkyl;
R$^{13}$ and R$^{14}$ are independently selected from the group consisting of hydrogen, C$_1$-C$_6$ alkyl, and (CH$_2$)$_n$R$^{15}$ wherein R$^{15}$ is NR$^{16}$R$^{17}$, wherein R$^{16}$ and R$^{17}$ are independently selected from the group consisting of hydrogen, C$_1$-C$_6$ alkyl, and COR$^{18}$ wherein R$^{18}$ is hydrogen or C$_1$-C$_6$ alkyl; wherein n is an integer from 1 to 10;
R$^7$ is selected from the group consisting of bromo, chloro, iodo, C$_1$-C$_{20}$ alkyl, C$_7$-C$_{12}$ cycloalkyl C$_1$-C$_{20}$ alkyl, C$_7$-C$_{12}$ bicycloalkyl C$_1$-C$_{20}$ alkyl, C$_7$-C$_{12}$ bicycloalkenyl C$_1$-C$_{20}$ alkyl, C$_6$-C$_{14}$ aryl C$_1$-C$_{20}$ alkyl, C$_2$-C$_{20}$ alkenyl, C$_7$-C$_{12}$ cycloalkyl C$_2$-C$_{20}$ alkenyl, C$_7$-C$_{12}$ bicycloalkyl C$_2$-C$_{20}$ alkenyl, C$_7$-C$_{12}$ bicycloalkenyl C$_2$-C$_{20}$ alkenyl, C$_6$-C$_{14}$ aryl C$_2$-C$_{20}$ alkenyl, C$_2$-C$_{20}$ alkynyl, C$_7$-C$_{12}$ cycloalkyl C$_2$-C$_{20}$ alkynyl, C$_7$-C$_{12}$ bicycloalkyl C$_2$-C$_{20}$ alkynyl, C$_7$-C$_{12}$ bicycloalkenyl C$_2$-C$_{20}$ alkynyl, and C$_6$-C$_{14}$ aryl C$_2$-C$_{20}$ alkynyl, and the alkyl, cycloalkyl, or aryl portion of R$^7$ is optionally substituted with one or more substituents selected from the group consisting of halo, hydroxyl, amino, alkylamino, dialkylamino, mercapto, carboxy, alkoxycarbonyl, aminocarbonyl, alkylaminocarbonyl, dialkylaminocarbonyl, aminoalkylaminocarbonyl, trialkylsilyl, and any combination thereof;
R$^8$ and R$^9$ are independently selected from the group consisting of hydroxyl, amino, mercapto, ureido, C$_1$-C$_6$ alkyl carbonylamino, hydroxy C$_1$-C$_6$ alkyl, and hydrazinyl; and
R$^{19}$ is selected from the group consisting of C$_1$-C$_3$ alkyl aminocarbonyl, di(C$_1$-C$_3$ alkyl)aminocarbonyl, C$_1$-C$_3$ alkylthio C$_1$-C$_3$ alkyl, halo C$_1$-C$_3$ alkyl, hydrazinyl, amino C$_1$-C$_3$ alkyl, hydroxy C$_1$-C$_3$ alkyl, C$_3$-C$_6$ cycloalkylamino, hydroxylamino, and C$_2$-C$_3$ alkenyl;
or a pharmaceutically acceptable salt thereof.

20. The compound of claim 19, wherein R$^6$ is benzyl substituted with C≡C—(CH$_2$)$_n$—COR$^{11}$, wherein R$^{11}$ is selected from the group consisting of OH, OR$^{12}$, and NR$^{13}$R$^{14}$, and wherein n is an integer of 1 to 10, or a pharmaceutically acceptable salt thereof.

21. The compound of claim 20, wherein R$^{11}$ is OR$^{12}$ and wherein R$^{12}$ is C$_1$-C$_6$ alkyl, or a pharmaceutically acceptable salt thereof.

22. The compound of claim 20, wherein R$^{11}$ is NR$^{13}$R$^{14}$ and wherein R$^{13}$ and R$^{14}$ are both hydrogen, or a pharmaceutically acceptable salt thereof.

23. The compound of claim 20, wherein R$^{11}$ is NR$^{13}$R$^{14}$, wherein R$^{13}$ is hydrogen, wherein R$^{14}$ is (CH$_2$)$_n$R$^{15}$, and wherein R$^{15}$ is NR$^{16}$R$^{17}$, or a pharmaceutically acceptable salt thereof.

24. The compound of claim 19, wherein R$^7$ is selected from the group consisting of chloro, bromo, iodo, C$_2$-C$_{20}$ alkynyl, C$_7$-C$_{12}$ cycloalkyl C$_2$-C$_{20}$ alkynyl, C$_7$-C$_{12}$ bicycloalkyl C$_2$-C$_{20}$ alkynyl, C$_7$-C$_{12}$ bicycloalkenyl C$_2$-C$_{20}$ alkynyl, and C$_6$-C$_{14}$ aryl C$_2$-C$_{20}$ alkynyl, or a pharmaceutically acceptable salt thereof.

25. The compound of claim 19, wherein R$^8$ and R$^9$ are independently selected from the group consisting of hydroxyl, amino, mercapto, and ureido, or a pharmaceutically acceptable salt thereof.

26. The compound of claim 19, wherein R$^{10}$ is selected from the group consisting of C$_1$-C$_3$ alkyl aminocarbonyl, di(C$_1$-C$_3$ alkyl)aminocarbonyl, C$_3$ alkylthio C$_1$-C$_3$ alkyl, halo C$_1$-C$_3$ alkyl, amino C$_1$-C$_3$ alkyl, hydroxy C$_1$-C$_3$ alkyl, and C$_3$-C$_6$ cycloalkylamino, or a pharmaceutically acceptable salt thereof.

27. The compound of claim 26, wherein R$^{10}$ is C$_1$-C$_3$ alkyl aminocarbonyl or di(C$_1$-C$_3$ alkyl)aminocarbonyl, or a pharmaceutically acceptable salt thereof.

28. The compound of claim 27, wherein R$^{10}$ is methylaminocarbonyl, or a pharmaceutically acceptable salt thereof.

29. The compound of claim 19, wherein R$^6$ is 3-(5-carboxy-1-pentynyl)benzyl, 3-(5-(2-aminoethyl)aminocarbonyl-1-pentynyl)benzyl, or 3-(5-(2-acetamidoethyl)aminocarbonyl-1-pentynyl)benzyl, R$^7$ is chloro, R$^8$ and R$^9$ are hydroxyl, and R$^{10}$ is methylamino carbonyl, or a pharmaceutically acceptable salt thereof.

30. A pharmaceutical composition comprising a compound of claim 1 or a pharmaceutically acceptable salt thereof and a pharmaceutically acceptable carrier.

31. A method for activating an A$_3$ adenosine receptor in a mammal comprising administering to the mammal an effective amount of a compound of claim 1 or a pharmaceutically acceptable salt thereof.

32. A method for activating an A$_3$ adenosine receptor in a cell comprising contacting said cell with a compound of claim 1 or a pharmaceutically acceptable salt thereof.

33. A method for activating A$_3$ adenosine receptors in a mammal comprising administering to the mammal an effective amount of a compound of claim 19 or a pharmaceutically acceptable salt thereof.

34. A pharmaceutical composition comprising a compound of claim 19 or a pharmaceutically acceptable salt thereof and a pharmaceutically acceptable carrier.

35. A method for activating an A$_3$ adenosine receptor in a mammal comprising administering to the mammal an effective amount of a compound of claim 19 or a pharmaceutically acceptable salt thereof.

* * * * *